US011230701B2

(12) United States Patent
Kinooka et al.

(10) Patent No.: US 11,230,701 B2
(45) Date of Patent: Jan. 25, 2022

(54) MUTANT HEMAGGLUTININ COMPLEX PROTEIN, AND METHOD FOR CULTURING PLURIPOTENT STEM CELLS USING SAME

(71) Applicant: Osaka University, Osaka (JP)

(72) Inventors: Masahiro Kinooka, Osaka (JP); Meehae Kim, Osaka (JP); Yukako Fujinaga, Osaka (JP); Yo Sugawara, Osaka (JP)

(73) Assignee: Osaka University, Osaka (JP)

( * ) Notice: Subject to any disclaimer, the term of this patent is extended or adjusted under 35 U.S.C. 154(b) by 1118 days.

(21) Appl. No.: 15/321,835

(22) PCT Filed: Jun. 29, 2015

(86) PCT No.: PCT/JP2015/068715

§ 371 (c)(1),
(2) Date: Dec. 23, 2016

(87) PCT Pub. No.: WO2015/199243

PCT Pub. Date: Dec. 30, 2015

(65) Prior Publication Data

US 2017/0130206 A1 May 11, 2017

(30) Foreign Application Priority Data

Jun. 27, 2014 (JP) ............................ JP2014-133364

(51) Int. Cl.

| | |
|---|---|
| ***C12N 5/074*** | (2010.01) |
| ***C07K 14/33*** | (2006.01) |
| ***C07K 19/00*** | (2006.01) |
| ***C12N 15/09*** | (2006.01) |
| ***C12N 5/10*** | (2006.01) |
| ***C12N 1/00*** | (2006.01) |
| ***C12N 5/00*** | (2006.01) |

(52) U.S. Cl.

CPC ............ *C12N 5/0696* (2013.01); *C07K 14/33* (2013.01); *C07K 19/00* (2013.01); *C12N 1/00* (2013.01); *C12N 5/0081* (2013.01); *C12N 5/10* (2013.01); *C12N 15/09* (2013.01); *C12N 2501/998* (2013.01)

(58) Field of Classification Search

None

See application file for complete search history.

(56) References Cited

U.S. PATENT DOCUMENTS

| | | | |
|---|---|---|---|
| 2011/0053244 A1 | 3/2011 | Oyler et al. |
| 2012/0164729 A1 | 6/2012 | Tomizawa |
| 2015/0306214 A1 | 10/2015 | Fujinaga et al. |
| 2015/0329831 A1 | 11/2015 | Kinooka et al. |

FOREIGN PATENT DOCUMENTS

| | | | |
|---|---|---|---|
| JP | 2007-511609 A | 5/2007 |
| JP | 2008-169166 A | 7/2008 |
| JP | 2012-143229 A | 8/2012 |
| WO | 2005/048949 A2 | 6/2005 |
| WO | 2013/013105 A2 | 1/2013 |
| WO | 2014/087849 A1 | 6/2014 |
| WO | 2014/104207 A1 | 7/2014 |

OTHER PUBLICATIONS

Amatsu, S. et al., JBC, 2013, vol. 288: pp. 35617-35625.*
Vector Information, pET28b(+), Plasmid Repository, 2 pages, printed 2020.*
Fujinaga et al., "Elucidation of Mechanism of Intestinal Absorption-Promoting Effect of Botulinum Toxin Complex and Development of Novel Drug Delivery System Using the Effect," Research Papers of the Suzuken Memorial Foundation 2009, 28: 298-301 (2011) (partial English translation).
Sugawara et al., "Botulinum hemagglutinin disrupts the intercellular epithelial barrier by directly binding E-cadherin," Journal of Cell Biology, 189: 691-700 (2010).
Kim et al., "Removing cells which deviate from undifferentiated state of human iPS by using hemagglutin derived from botulinum," Regenerative Medicine, 14: 326 (2015) (cited in ISR issued in corresponding PCT/JP2015/068715).
Sugawara et al., "Functional Dissection of the Clostridium botulinum Type B Hemagglutinin Complex: Identification of the Carbohydrate and E-Cadherin Binding Sites," PLOS One, 9: e111170 (2014).
International Search Report issued in corresponding International Patent Application No. PCT/JP2015/068715 dated Sep. 15, 2015.
Lee et al., "High-resolution crystal structure of HA33 of botulinum neurotoxin type B progenitor toxin complex," Biochemical and Biophysical Research Communications, 446: 568-573 (2014).
Lee et al., "Molecular basis for disruption of E-cadherin adhesion by botulinum neurotoxin A complex," Science, 344: 1405-1410 (2014).
Matsumura et al., "Botulinum toxin A complex exploits intestinal M cells to enter the host and exert neurotoxicity," Nature Communications, 6: 6255 (2015).
Mohamet et al., "Abrogation of E-Cadherin-Mediated Cellular Aggregation Allows Proliferation of Pluripotent Mouse Embryonic Stem Cells in Shake Flask Bioreactors," PLOS One, 5: e12921 (2010).

(Continued)

*Primary Examiner* — Michael D Burkhart
(74) *Attorney, Agent, or Firm* — Morgan, Lewis & Bockius LLP

(57) ABSTRACT

Provided are a novel hemagglutinin that can remove cells deviated from the undifferentiated state, the cells being cells that emerge in a colony during culture of stem cells having pluripotency, and a novel method for culturing stem cells having pluripotency, the method using hemagglutinin. Provided is a mutant hemagglutinin complex protein derived from *Clostridium botulinum* type B, the complex protein containing at least subcomponents HA2 and HA3 of hemagglutinin derived from *Clostridium botulinum* type B, and the complex protein containing amino acids constituting a glycosylation site, with at least one of the amino acids having been mutated. Provided is a method for culturing stem cells having pluripotency, the method including culturing the stem cell having pluriopotency in the presence of a mutant hemagglutinin complex protein of the present disclosure.

18 Claims, 12 Drawing Sheets

Specification includes a Sequence Listing.

(56) References Cited

OTHER PUBLICATIONS

Kim et al., "Kinetic Analysis of Deviation From the Undifferentiated State in Colonies of Human Induced Pluripotent Stem Cells on Feeder Layers," Biotechnology and Bioengineering, 111: 1128-1138 (2014).
Inoue et al., "Structural analysis by X-ray crystallography and calorimetry of a haemagglutinin component (HA1) of the progenitor toxin from Clostridium botulinum," Microbiology, 149: 3361-3370 (2003).
Jin et al., "Disruption of the epithelial barrier by botulinum haemagglutinin (HA) proteins—differences in cell tropism and the mechanism of action between HA proteins of types A or B, and HA proteins of type C," Microbiology, 155: 35-45 (2009).
Sugawara et al., "The botulinum toxin complex meets E-cadherin on the way to its destination," Cell Adhesion & Migration, 5: 34-36 (2011).
Yamashita et al., "Carbohydrate Recognition Mechanism of HA70 from Clostridium Botulinum Deduced from X-Ray Structures in Complexes with Sialylated Oligosaccharides," Kagawa University, retrieved from http://www.kms.ac.jp/~xraylab/report/poster/HA3.pdf (2012).
Hasegawa et al., "Protein Structure and Folding: A Novel Subunit Structure of Clostridium botulinum Serotype D Toxin Complex with Three Extended Arms," Journal of Biological Chemistry, 282: 24777-24783 (2007).
Lee et al., "Structure of a Bimodular Botulinum Neurotoxin Complex Provides Insights into Its Oral Toxicity," PLOS Pathogens, 9: e1003690 (2013).
Partial Supplementary European Search Report issued in corresponding European Patent Application No. 15811956.0 dated Oct. 24, 2017.

* cited by examiner

Effect of Type B Wild-Type and Type B Mutant HA Complexes on iPS Cells (300 cells/well)

100nM Type A Mutant HA Complex 3 (HA1 N285A/HA3 R528A)  ▨ Deviated Cell Area

100nM Type A Mutant HA Complex 4 (HA3 K607A)  ▨ Deviated Cell Area

SEQUENCE LISTING

```
<160> NUMBER OF SEQ ID NOS: 18

<210> SEQ ID NO 1
<211> LENGTH: 294
<212> TYPE: PRT
<213> ORGANISM: Clostridium botulinum

<400> SEQUENCE: 1

Met Glu His Tyr Ser Thr Ile Gln Asn Ser Leu Asn Asp Lys Ile Val
1               5                   10                  15

Thr Ile Ser Cys Lys Ala Asn Thr Asp Leu Phe Phe Tyr Gln Val Pro
            20                  25                  30

Gly Asn Gly Asn Val Ser Leu Phe Gln Gln Thr Arg Asn Tyr Leu Glu
        35                  40                  45

Arg Trp Arg Ile Ile Tyr Asp Ser Asn Lys Ala Ala Tyr Lys Ile Lys
    50                  55                  60

Ser Met Asn Ile Tyr Asn Thr Asn Leu Val Leu Thr Trp Asn Ala Pro
65                  70                  75                  80

Thr His Asn Ile Ser Ala Gln Gln Asp Ser Asn Ala Asp Asn Gln Tyr
                85                  90                  95

Trp Leu Leu Leu Lys Asp Ile Gly Asn Asn Ser Phe Ile Ile Ala Ser
            100                 105                 110

Tyr Lys Asn Pro Asn Leu Val Leu Tyr Ala Asp Thr Val Ala Arg Asn
        115                 120                 125

Leu Lys Leu Ser Thr Leu Asn Asn Ser Ser Tyr Ile Lys Phe Ile Ile
```

```
    130                 135                 140

Glu Asp Tyr Val Ile Ser Asp Phe Lys Asn Phe Thr Cys Arg Ile Ser
145                 150                 155                 160

Pro Ile Leu Ala Gly Gly Lys Val Val Gln Gln Val Ser Met Thr Asn
                165                 170                 175

Leu Ala Val Asn Leu Tyr Ile Trp Asn Asn Asp Leu Asn Gln Lys Trp
            180                 185                 190

Thr Ile Ile Tyr Asn Glu Glu Lys Ala Ala Tyr Gln Phe Phe Asn Lys
        195                 200                 205

Ile Leu Ser Asn Gly Val Leu Thr Trp Ile Phe Ser Asp Gly Asn Thr
    210                 215                 220

Val Arg Val Ser Ser Ser Ala Gln Asn Asn Asp Ala Gln Tyr Trp Leu
225                 230                 235                 240

Ile Asn Pro Val Ser Asp Asn Tyr Asp Arg Tyr Thr Ile Thr Asn Leu
                245                 250                 255

Arg Asp Lys Thr Lys Val Leu Asp Leu Tyr Gly Gly Gln Thr Ala Asp
            260                 265                 270

Gly Thr Thr Ile Gln Val Phe Asn Ser Asn Gly Gly Asp Asn Gln Ile
        275                 280                 285

Trp Thr Met Ser Asn Pro
    290


<210> SEQ ID NO 2
<211> LENGTH: 146
<212> TYPE: PRT
<213> ORGANISM: Clostridium botulinum

<400> SEQUENCE: 2

Met Ser Ala Glu Arg Thr Phe Leu Pro Asn Gly Asn Tyr Asn Ile Lys
1               5                   10                  15

Ser Ile Phe Ser Gly Ser Leu Tyr Leu Ser Pro Val Ser Gly Ser Leu
            20                  25                  30

Thr Phe Ser Asn Glu Ser Ser Ala Asn Asn Gln Lys Trp Asn Val Glu
        35                  40                  45

Tyr Met Ala Glu Asn Arg Cys Phe Lys Ile Ser Asn Val Ala Glu Pro
    50                  55                  60

Asn Lys Tyr Leu Ser Tyr Asp Asn Phe Gly Phe Ile Ser Leu Asp Ser
65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
            100                 105                 110

Asp Ile Tyr Asp Thr Asn Glu Asn Ile Leu Ser Gln Pro Leu Leu Leu
        115                 120                 125

Leu Pro Asn Phe Asp Ile Tyr Asn Ser Asn Gln Met Phe Lys Leu Glu
    130                 135                 140

Lys Ile
145


<210> SEQ ID NO 3
<211> LENGTH: 626
<212> TYPE: PRT
<213> ORGANISM: Clostridium botulinum

<400> SEQUENCE: 3

Met Asn Ser Ser Ile Lys Lys Ile Tyr Asn His Ile Gln Glu Lys Val
```

-continued 1 5 10 15

Ile Asn Tyr Ser Asp Thr Ile Asp Leu Ala Asp Gly Asn Tyr Val Val
20 25 30

Ser Arg Gly Asp Gly Trp Ile Leu Ser Arg Gln Asn Gln Ile Leu Gly
35 40 45

Gly Ser Val Ile Ser Asn Gly Ser Thr Gly Ile Val Gly Asp Leu Arg
50 55 60

Val Asn Asp Asn Ala Ile Pro Tyr Tyr Tyr Pro Thr Pro Ser Phe Asn
65 70 75 80

Glu Glu Tyr Ile Lys Asn Asn Ile Gln Thr Val Phe Ala Asn Phe Thr
85 90 95

Glu Ala Asn Gln Ile Pro Ile Gly Phe Glu Phe Ser Lys Thr Ala Pro
100 105 110

Ser Asn Lys Asn Leu Tyr Met Tyr Leu Gln Tyr Thr Tyr Ile Arg Tyr
115 120 125

Glu Ile Ile Lys Val Leu Gln His Glu Ile Ile Glu Arg Ala Val Leu
130 135 140

Tyr Val Pro Ser Leu Gly Tyr Val Lys Ser Ile Glu Phe Asn Pro Gly
145 150 155 160

Glu Lys Ile Asn Lys Asp Phe Tyr Phe Leu Thr Asn Asp Lys Cys Ile
165 170 175

Leu Asn Glu Gln Phe Leu Tyr Lys Lys Ile Leu Glu Thr Thr Lys Asn
180 185 190

Ile Pro Thr Asn Asn Ile Phe Asn Ser Lys Val Ser Ser Thr Gln Arg
195 200 205

Val Leu Pro Tyr Ser Asn Gly Leu Tyr Val Ile Asn Lys Gly Asp Gly
210 215 220

Tyr Ile Arg Thr Asn Asp Lys Asp Leu Ile Gly Thr Leu Leu Ile Glu
225 230 235 240

Ala Gly Ser Ser Gly Ser Ile Ile Gln Pro Arg Leu Arg Asn Thr Thr
245 250 255

Arg Pro Leu Phe Thr Thr Ser Asn Asp Ala Lys Phe Ser Gln Gln Tyr
260 265 270

Thr Glu Glu Arg Leu Lys Asp Ala Phe Asn Val Gln Leu Phe Asn Thr
275 280 285

Ser Thr Ser Leu Phe Lys Phe Val Glu Glu Ala Pro Ser Asn Lys Asn
290 295 300

Ile Cys Ile Lys Ala Tyr Asn Thr Tyr Glu Lys Tyr Glu Leu Ile Asp
305 310 315 320

Tyr Gln Asn Gly Ser Ile Val Asn Lys Ala Glu Tyr Tyr Leu Pro Ser
325 330 335

Leu Gly Tyr Cys Glu Val Thr Asn Ala Pro Ser Pro Glu Ser Glu Val
340 345 350

Val Lys Thr Gln Val Ala Glu Asp Gly Phe Ile Gln Asn Gly Pro Glu
355 360 365

Glu Glu Ile Val Val Gly Val Ile Asp Pro Ser Glu Asn Ile Gln Glu
370 375 380

Ile Asn Thr Ala Ile Ser Asp Asn Tyr Thr Tyr Asn Ile Pro Gly Ile
385 390 395 400

Val Asn Asn Asn Pro Phe Tyr Ile Leu Phe Thr Val Asn Thr Thr Gly
405 410 415

Ile Tyr Lys Ile Asn Ala Gln Asn Asn Leu Pro Ser Leu Lys Ile Tyr
420 425 430

-continued

Glu Ala Ile Gly Ser Gly Asn Arg Asn Phe Gln Ser Gly Asn Leu Cys
        435                 440                 445

Asp Asp Asp Ile Lys Ala Ile Asn Tyr Ile Thr Gly Phe Asp Ser Pro
    450                 455                 460

Asn Ala Lys Ser Tyr Leu Val Val Leu Leu Asn Lys Asp Lys Asn Tyr
465                 470                 475                 480

Tyr Ile Arg Val Pro Gln Thr Ser Ser Asn Ile Glu Asn Gln Ile Lys
                485                 490                 495

Phe Lys Arg Glu Glu Gly Asp Leu Arg Asn Leu Met Asn Ser Ser Val
            500                 505                 510

Asn Ile Ile Asp Asn Leu Asn Ser Thr Gly Ala His Tyr Tyr Thr Arg
        515                 520                 525

Gln Ser Pro Asp Val His Asp Tyr Ile Ser Tyr Glu Phe Thr Ile Pro
    530                 535                 540

Gly Asn Phe Asn Asn Lys Asp Thr Ser Asn Ile Arg Leu Tyr Thr Ser
545                 550                 555                 560

Tyr Asn Gln Gly Ile Gly Thr Leu Phe Arg Val Thr Glu Thr Ile Asp
                565                 570                 575

Gly Tyr Asn Leu Ile Asn Ile Gln Gln Asn Leu Asn Leu Leu Asn Ser
            580                 585                 590

Thr Lys Ser Ile Arg Leu Leu Asn Gly Ala Ile Tyr Ile Leu Lys Val
        595                 600                 605

Glu Val Thr Glu Leu Asn Asn Tyr Asn Ile Lys Leu His Ile Asp Ile
    610                 615                 620

Thr Asn
625

<210> SEQ ID NO 4
<211> LENGTH: 294
<212> TYPE: PRT
<213> ORGANISM: Artificial Sequence
<220> FEATURE:
<223> OTHER INFORMATION: HA1 N286A

<400> SEQUENCE: 4

Met Glu His Tyr Ser Thr Ile Gln Asn Ser Leu Asn Asp Lys Ile Val
1               5                   10                  15

Thr Ile Ser Cys Lys Ala Asn Thr Asp Leu Phe Phe Tyr Gln Val Pro
            20                  25                  30

Gly Asn Gly Asn Val Ser Leu Phe Gln Gln Thr Arg Asn Tyr Leu Glu
        35                  40                  45

Arg Trp Arg Ile Ile Tyr Asp Ser Asn Lys Ala Ala Tyr Lys Ile Lys
    50                  55                  60

Ser Met Asn Ile Tyr Asn Thr Asn Leu Val Leu Thr Trp Asn Ala Pro
65                  70                  75                  80

Thr His Asn Ile Ser Ala Gln Gln Asp Ser Asn Ala Asp Asn Gln Tyr
                85                  90                  95

Trp Leu Leu Leu Lys Asp Ile Gly Asn Asn Ser Phe Ile Ile Ala Ser
            100                 105                 110

Tyr Lys Asn Pro Asn Leu Val Leu Tyr Ala Asp Thr Val Ala Arg Asn
        115                 120                 125

Leu Lys Leu Ser Thr Leu Asn Asn Ser Ser Tyr Ile Lys Phe Ile Ile
    130                 135                 140

Glu Asp Tyr Val Ile Ser Asp Phe Lys Asn Phe Thr Cys Arg Ile Ser
145                 150                 155                 160

-continued

Pro Ile Leu Ala Gly Gly Lys Val Val Gln Gln Val Ser Met Thr Asn
165 170 175

Leu Ala Val Asn Leu Tyr Ile Trp Asn Asn Asp Leu Asn Gln Lys Trp
180 185 190

Thr Ile Ile Tyr Asn Glu Glu Lys Ala Ala Tyr Gln Phe Phe Asn Lys
195 200 205

Ile Leu Ser Asn Gly Val Leu Thr Trp Ile Phe Ser Asp Gly Asn Thr
210 215 220

Val Arg Val Ser Ser Ser Ala Gln Asn Asn Asp Ala Gln Tyr Trp Leu
225 230 235 240

Ile Asn Pro Val Ser Asp Asn Tyr Asp Arg Tyr Thr Ile Thr Asn Leu
245 250 255

Arg Asp Lys Thr Lys Val Leu Asp Leu Tyr Gly Gly Gln Thr Ala Asp
260 265 270

Gly Thr Thr Ile Gln Val Phe Asn Ser Asn Gly Gly Asp Ala Gln Ile
275 280 285

Trp Thr Met Ser Asn Pro
290

<210> SEQ ID NO 5
<211> LENGTH: 626
<212> TYPE: PRT
<213> ORGANISM: Artificial Sequence
<220> FEATURE:
<223> OTHER INFORMATION: HA3 R528A

<400> SEQUENCE: 5

Met Asn Ser Ser Ile Lys Lys Ile Tyr Asn His Ile Gln Glu Lys Val
1 5 10 15

Ile Asn Tyr Ser Asp Thr Ile Asp Leu Ala Asp Gly Asn Tyr Val Val
20 25 30

Ser Arg Gly Asp Gly Trp Ile Leu Ser Arg Gln Asn Gln Ile Leu Gly
35 40 45

Gly Ser Val Ile Ser Asn Gly Ser Thr Gly Ile Val Gly Asp Leu Arg
50 55 60

Val Asn Asp Asn Ala Ile Pro Tyr Tyr Tyr Pro Thr Pro Ser Phe Asn
65 70 75 80

Glu Glu Tyr Ile Lys Asn Asn Ile Gln Thr Val Phe Ala Asn Phe Thr
85 90 95

Glu Ala Asn Gln Ile Pro Ile Gly Phe Glu Phe Ser Lys Thr Ala Pro
100 105 110

Ser Asn Lys Asn Leu Tyr Met Tyr Leu Gln Tyr Thr Tyr Ile Arg Tyr
115 120 125

Glu Ile Ile Lys Val Leu Gln His Glu Ile Ile Glu Arg Ala Val Leu
130 135 140

Tyr Val Pro Ser Leu Gly Tyr Val Lys Ser Ile Glu Phe Asn Pro Gly
145 150 155 160

Glu Lys Ile Asn Lys Asp Phe Tyr Phe Leu Thr Asn Asp Lys Cys Ile
165 170 175

Leu Asn Glu Gln Phe Leu Tyr Lys Lys Ile Leu Glu Thr Thr Lys Asn
180 185 190

Ile Pro Thr Asn Asn Ile Phe Asn Ser Lys Val Ser Ser Thr Gln Arg
195 200 205

Val Leu Pro Tyr Ser Asn Gly Leu Tyr Val Ile Asn Lys Gly Asp Gly
210 215 220

-continued

```
Tyr Ile Arg Thr Asn Asp Lys Asp Leu Ile Gly Thr Leu Leu Ile Glu
225                 230                 235                 240

Ala Gly Ser Ser Gly Ser Ile Ile Gln Pro Arg Leu Arg Asn Thr Thr
                245                 250                 255

Arg Pro Leu Phe Thr Thr Ser Asn Asp Ala Lys Phe Ser Gln Gln Tyr
            260                 265                 270

Thr Glu Glu Arg Leu Lys Asp Ala Phe Asn Val Gln Leu Phe Asn Thr
        275                 280                 285

Ser Thr Ser Leu Phe Lys Phe Val Glu Glu Ala Pro Ser Asn Lys Asn
    290                 295                 300

Ile Cys Ile Lys Ala Tyr Asn Thr Tyr Glu Lys Tyr Glu Leu Ile Asp
305                 310                 315                 320

Tyr Gln Asn Gly Ser Ile Val Asn Lys Ala Glu Tyr Tyr Leu Pro Ser
                325                 330                 335

Leu Gly Tyr Cys Glu Val Thr Asn Ala Pro Ser Pro Glu Ser Glu Val
            340                 345                 350

Val Lys Thr Gln Val Ala Glu Asp Gly Phe Ile Gln Asn Gly Pro Glu
        355                 360                 365

Glu Glu Ile Val Val Gly Val Ile Asp Pro Ser Glu Asn Ile Gln Glu
    370                 375                 380

Ile Asn Thr Ala Ile Ser Asp Asn Tyr Thr Tyr Asn Ile Pro Gly Ile
385                 390                 395                 400

Val Asn Asn Asn Pro Phe Tyr Ile Leu Phe Thr Val Asn Thr Thr Gly
                405                 410                 415

Ile Tyr Lys Ile Asn Ala Gln Asn Asn Leu Pro Ser Leu Lys Ile Tyr
            420                 425                 430

Glu Ala Ile Gly Ser Gly Asn Arg Asn Phe Gln Ser Gly Asn Leu Cys
        435                 440                 445

Asp Asp Asp Ile Lys Ala Ile Asn Tyr Ile Thr Gly Phe Asp Ser Pro
    450                 455                 460

Asn Ala Lys Ser Tyr Leu Val Val Leu Leu Asn Lys Asp Lys Asn Tyr
465                 470                 475                 480

Tyr Ile Arg Val Pro Gln Thr Ser Ser Asn Ile Glu Asn Gln Ile Lys
                485                 490                 495

Phe Lys Arg Glu Glu Gly Asp Leu Arg Asn Leu Met Asn Ser Ser Val
            500                 505                 510

Asn Ile Ile Asp Asn Leu Asn Ser Thr Gly Ala His Tyr Tyr Thr Ala
        515                 520                 525

Gln Ser Pro Asp Val His Asp Tyr Ile Ser Tyr Glu Phe Thr Ile Pro
    530                 535                 540

Gly Asn Phe Asn Asn Lys Asp Thr Ser Asn Ile Arg Leu Tyr Thr Ser
545                 550                 555                 560

Tyr Asn Gln Gly Ile Gly Thr Leu Phe Arg Val Thr Glu Thr Ile Asp
                565                 570                 575

Gly Tyr Asn Leu Ile Asn Ile Gln Gln Asn Leu Asn Leu Leu Asn Ser
            580                 585                 590

Thr Lys Ser Ile Arg Leu Leu Asn Gly Ala Ile Tyr Ile Leu Lys Val
        595                 600                 605

Glu Val Thr Glu Leu Asn Asn Tyr Asn Ile Lys Leu His Ile Asp Ile
    610                 615                 620

Thr Asn
625
```

-continued

<210> SEQ ID NO 6
<211> LENGTH: 626
<212> TYPE: PRT
<213> ORGANISM: Artificial Sequence
<220> FEATURE:
<223> OTHER INFORMATION: HA3 K607A

<400> SEQUENCE: 6

```
Met Asn Ser Ser Ile Lys Lys Ile Tyr Asn His Ile Gln Glu Lys Val
1               5                   10                  15

Ile Asn Tyr Ser Asp Thr Ile Asp Leu Ala Asp Gly Asn Tyr Val Val
            20                  25                  30

Ser Arg Gly Asp Gly Trp Ile Leu Ser Arg Gln Asn Gln Ile Leu Gly
        35                  40                  45

Gly Ser Val Ile Ser Asn Gly Ser Thr Gly Ile Val Gly Asp Leu Arg
    50                  55                  60

Val Asn Asp Asn Ala Ile Pro Tyr Tyr Tyr Pro Thr Pro Ser Phe Asn
65                  70                  75                  80

Glu Glu Tyr Ile Lys Asn Asn Ile Gln Thr Val Phe Ala Asn Phe Thr
                85                  90                  95

Glu Ala Asn Gln Ile Pro Ile Gly Phe Glu Phe Ser Lys Thr Ala Pro
            100                 105                 110

Ser Asn Lys Asn Leu Tyr Met Tyr Leu Gln Tyr Thr Tyr Ile Arg Tyr
        115                 120                 125

Glu Ile Ile Lys Val Leu Gln His Glu Ile Ile Glu Arg Ala Val Leu
    130                 135                 140

Tyr Val Pro Ser Leu Gly Tyr Val Lys Ser Ile Glu Phe Asn Pro Gly
145                 150                 155                 160

Glu Lys Ile Asn Lys Asp Phe Tyr Phe Leu Thr Asn Asp Lys Cys Ile
                165                 170                 175

Leu Asn Glu Gln Phe Leu Tyr Lys Lys Ile Leu Glu Thr Thr Lys Asn
            180                 185                 190

Ile Pro Thr Asn Asn Ile Phe Asn Ser Lys Val Ser Ser Thr Gln Arg
        195                 200                 205

Val Leu Pro Tyr Ser Asn Gly Leu Tyr Val Ile Asn Lys Gly Asp Gly
    210                 215                 220

Tyr Ile Arg Thr Asn Asp Lys Asp Leu Ile Gly Thr Leu Leu Ile Glu
225                 230                 235                 240

Ala Gly Ser Ser Gly Ser Ile Ile Gln Pro Arg Leu Arg Asn Thr Thr
                245                 250                 255

Arg Pro Leu Phe Thr Thr Ser Asn Asp Ala Lys Phe Ser Gln Gln Tyr
            260                 265                 270

Thr Glu Glu Arg Leu Lys Asp Ala Phe Asn Val Gln Leu Phe Asn Thr
        275                 280                 285

Ser Thr Ser Leu Phe Lys Phe Val Glu Glu Ala Pro Ser Asn Lys Asn
    290                 295                 300

Ile Cys Ile Lys Ala Tyr Asn Thr Tyr Glu Lys Tyr Glu Leu Ile Asp
305                 310                 315                 320

Tyr Gln Asn Gly Ser Ile Val Asn Lys Ala Glu Tyr Tyr Leu Pro Ser
                325                 330                 335

Leu Gly Tyr Cys Glu Val Thr Asn Ala Pro Ser Pro Glu Ser Glu Val
            340                 345                 350

Val Lys Thr Gln Val Ala Glu Asp Gly Phe Ile Gln Asn Gly Pro Glu
        355                 360                 365
```

Glu Glu Ile Val Val Gly Val Ile Asp Pro Ser Glu Asn Ile Gln Glu
370 375 380

Ile Asn Thr Ala Ile Ser Asp Asn Tyr Thr Tyr Asn Ile Pro Gly Ile
385 390 395 400

Val Asn Asn Asn Pro Phe Tyr Ile Leu Phe Thr Val Asn Thr Thr Gly
405 410 415

Ile Tyr Lys Ile Asn Ala Gln Asn Asn Leu Pro Ser Leu Lys Ile Tyr
420 425 430

Glu Ala Ile Gly Ser Gly Asn Arg Asn Phe Gln Ser Gly Asn Leu Cys
435 440 445

Asp Asp Asp Ile Lys Ala Ile Asn Tyr Ile Thr Gly Phe Asp Ser Pro
450 455 460

Asn Ala Lys Ser Tyr Leu Val Val Leu Leu Asn Lys Asp Lys Asn Tyr
465 470 475 480

Tyr Ile Arg Val Pro Gln Thr Ser Ser Asn Ile Glu Asn Gln Ile Lys
485 490 495

Phe Lys Arg Glu Glu Gly Asp Leu Arg Asn Leu Met Asn Ser Ser Val
500 505 510

Asn Ile Ile Asp Asn Leu Asn Ser Thr Gly Ala His Tyr Tyr Thr Arg
515 520 525

Gln Ser Pro Asp Val His Asp Tyr Ile Ser Tyr Glu Phe Thr Ile Pro
530 535 540

Gly Asn Phe Asn Asn Lys Asp Thr Ser Asn Ile Arg Leu Tyr Thr Ser
545 550 555 560

Tyr Asn Gln Gly Ile Gly Thr Leu Phe Arg Val Thr Glu Thr Ile Asp
565 570 575

Gly Tyr Asn Leu Ile Asn Ile Gln Gln Asn Leu Asn Leu Leu Asn Ser
580 585 590

Thr Lys Ser Ile Arg Leu Leu Asn Gly Ala Ile Tyr Ile Leu Ala Val
595 600 605

Glu Val Thr Glu Leu Asn Asn Tyr Asn Ile Lys Leu His Ile Asp Ile
610 615 620

Thr Asn
625

<210> SEQ ID NO 7
<211> LENGTH: 8
<212> TYPE: PRT
<213> ORGANISM: Artificial Sequence
<220> FEATURE:
<223> OTHER INFORMATION: FLAG tag

<400> SEQUENCE: 7

Asp Tyr Lys Asp Asp Asp Asp Lys
1 5

<210> SEQ ID NO 8
<211> LENGTH: 8
<212> TYPE: PRT
<213> ORGANISM: Artificial Sequence
<220> FEATURE:
<223> OTHER INFORMATION: Strep tag

<400> SEQUENCE: 8

Trp Ser His Pro Gln Phe Glu Lys
1 5

<210> SEQ ID NO 9

<211> LENGTH: 33
<212> TYPE: DNA
<213> ORGANISM: Artificial Sequence
<220> FEATURE:
<223> OTHER INFORMATION: primer

<400> SEQUENCE: 9
catgccatgg gcatccaaaa ttcattaaat gac 33

<210> SEQ ID NO 10
<211> LENGTH: 57
<212> TYPE: DNA
<213> ORGANISM: Artificial Sequence
<220> FEATURE:
<223> OTHER INFORMATION: primer

<400> SEQUENCE: 10
cgggatcctt acttgtcgtc atcgtctttg tagtctgggt tactcatagt ccatatc 57

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
tgaataagct ttcagctgaa agaacttttc 30

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
cactttggta ccttatattt tttcaagttt ga 32

<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13
gaaaaagggt accaatatag tgatactatt g 31

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
cgtgtcgact taattagtaa tatctatatg c 31

<210> SEQ ID NO 15
<211> LENGTH: 4
<212> TYPE: PRT
<213> ORGANISM: Artificial Sequence
<220> FEATURE:
<223> OTHER INFORMATION: D4 tag

<400> SEQUENCE: 15

Asp Asp Asp Asp
1

<210> SEQ ID NO 16
<211> LENGTH: 293
<212> TYPE: PRT
<213> ORGANISM: Clostridium botulinum

<400> SEQUENCE: 16

Met Glu His Tyr Ser Val Ile Gln Asn Ser Leu Asn Asp Lys Ile Val
1 5 10 15

Thr Ile Ser Cys Lys Ala Asp Thr Asn Leu Phe Phe Tyr Gln Val Ala
20 25 30

Gly Asn Val Ser Leu Phe Gln Gln Thr Arg Asn Tyr Leu Glu Arg Trp
35 40 45

Arg Leu Ile Tyr Asp Ser Asn Lys Ala Ala Tyr Lys Ile Lys Ser Met
50 55 60

Asp Ile His Asn Thr Asn Leu Val Leu Thr Trp Asn Ala Pro Thr His
65 70 75 80

Asn Ile Ser Thr Gln Gln Asp Ser Asn Ala Asp Asn Gln Tyr Trp Leu
85 90 95

Leu Leu Lys Asp Ile Gly Asn Asn Ser Phe Ile Ile Ala Ser Tyr Lys
100 105 110

Asn Pro Asn Leu Val Leu Tyr Ala Asp Thr Val Ala Arg Asn Leu Lys
115 120 125

Leu Ser Thr Leu Asn Asn Ser Asn Tyr Ile Lys Phe Ile Ile Glu Asp
130 135 140

Tyr Ile Ile Ser Asp Leu Asn Asn Phe Thr Cys Lys Ile Ser Pro Ile
145 150 155 160

Leu Asp Leu Asn Lys Val Val Gln Gln Val Asp Val Thr Asn Leu Asn
165 170 175

Val Asn Leu Tyr Thr Trp Asp Tyr Gly Arg Asn Gln Lys Trp Thr Ile
180 185 190

Arg Tyr Asn Glu Glu Lys Ala Ala Tyr Gln Phe Phe Asn Thr Ile Leu
195 200 205

Ser Asn Gly Val Leu Thr Trp Ile Phe Ser Asn Gly Asn Thr Val Arg
210 215 220

Val Ser Ser Ser Asn Asp Gln Asn Asn Asp Ala Gln Tyr Trp Leu Ile
225 230 235 240

Asn Pro Val Ser Asp Thr Asp Glu Thr Tyr Thr Ile Thr Asn Leu Arg
245 250 255

Asp Thr Thr Lys Ala Leu Asp Leu Tyr Gly Gly Gln Thr Ala Asn Gly
260 265 270

Thr Ala Ile Gln Val Phe Asn Tyr His Gly Asp Asp Asn Gln Lys Trp
275 280 285

Asn Ile Arg Asn Pro
290

<210> SEQ ID NO 17
<211> LENGTH: 146
<212> TYPE: PRT
<213> ORGANISM: Clostridium botulinum

<400> SEQUENCE: 17

Met Ser Val Glu Arg Thr Phe Leu Pro Asn Gly Asn Tyr Asn Ile Lys
1 5 10 15

-continued

Ser Ile Phe Ser Gly Ser Leu Tyr Leu Asn Pro Val Ser Lys Ser Leu
20 25 30

Thr Phe Ser Asn Glu Ser Ser Ala Asn Asn Gln Lys Trp Asn Val Glu
35 40 45

Tyr Met Ala Glu Asn Arg Cys Phe Lys Ile Ser Asn Val Ala Glu Pro
50 55 60

Asn Lys Tyr Leu Ser Tyr Asp Asn Phe Gly Phe Ile Ser Leu Asp Ser
65 70 75 80

Leu Ser Asn Arg Cys Tyr Trp Phe Pro Ile Lys Ile Ala Val Asn Thr
85 90 95

Tyr Ile Met Leu Ser Leu Asn Lys Val Asn Glu Leu Asp Tyr Ala Trp
100 105 110

Asp Ile Tyr Asp Thr Asn Glu Asn Ile Leu Ser Gln Pro Leu Leu Leu
115 120 125

Leu Pro Asn Phe Asp Ile Tyr Asn Ser Asn Gln Met Phe Lys Leu Glu
130 135 140

Lys Ile
145

<210> SEQ ID NO 18
<211> LENGTH: 626
<212> TYPE: PRT
<213> ORGANISM: Clostridium botulinum

<400> SEQUENCE: 18

Met Asn Ser Ser Ile Lys Lys Ile Tyr Asn Asp Ile Gln Glu Lys Val
1 5 10 15

Ile Asn Tyr Ser Asp Thr Ile Asp Leu Ala Asp Gly Asn Tyr Val Val
20 25 30

Arg Arg Gly Asp Gly Trp Ile Leu Ser Arg Gln Asn Gln Ile Leu Gly
35 40 45

Gly Ser Val Ile Ser Asn Gly Ser Thr Gly Ile Val Gly Asp Leu Arg
50 55 60

Val Asn Asp Asn Ala Ile Pro Tyr Tyr Tyr Pro Thr Pro Ser Phe Asn
65 70 75 80

Glu Glu Tyr Ile Lys Asn Asn Ile Gln Thr Val Phe Thr Asn Phe Thr
85 90 95

Glu Ala Asn Gln Ile Pro Ile Gly Phe Glu Phe Ser Lys Thr Ala Pro
100 105 110

Ser Asn Lys Asn Leu Tyr Met Tyr Leu Gln Tyr Thr Tyr Ile Arg Tyr
115 120 125

Glu Ile Ile Lys Val Leu Gln His Glu Ile Ile Glu Arg Ala Val Leu
130 135 140

Tyr Val Pro Ser Leu Gly Tyr Val Lys Ser Ile Glu Phe Asn Pro Gly
145 150 155 160

Glu Lys Ile Asn Lys Asp Phe Tyr Phe Leu Thr Asn Asp Lys Cys Ile
165 170 175

Leu Asn Glu Gln Phe Leu Tyr Lys Lys Ile Leu Glu Thr Thr Lys Asn
180 185 190

Ile Pro Thr Asn Asn Ile Phe Asn Ser Lys Val Ser Ser Thr Gln Arg
195 200 205

Val Leu Pro Tyr Ser Asn Gly Leu Tyr Val Ile Asn Lys Gly Asp Gly
210 215 220

Tyr Ile Arg Thr Asn Asp Lys Asp Leu Ile Gly Thr Leu Leu Ile Glu

-continued

```
225                 230                 235                 240

Ala Gly Ser Ser Gly Ser Ile Ile Gln Pro Arg Leu Arg Asn Thr Thr
                245                 250                 255

Arg Pro Leu Phe Thr Thr Ser Asn Asp Thr Lys Phe Ser Gln Gln Tyr
            260                 265                 270

Thr Glu Glu Arg Leu Lys Asp Ala Phe Asn Val Gln Leu Phe Asn Thr
        275                 280                 285

Ser Thr Ser Leu Phe Lys Phe Val Glu Glu Ala Pro Ser Asp Lys Asn
    290                 295                 300

Ile Cys Ile Lys Ala Tyr Asn Thr Tyr Glu Lys Tyr Glu Leu Ile Asp
305                 310                 315                 320

Tyr Gln Asn Gly Ser Ile Val Asn Lys Ala Glu Tyr Tyr Leu Pro Ser
                325                 330                 335

Leu Gly Tyr Cys Glu Val Thr Asn Ala Pro Ser Pro Glu Ser Glu Val
            340                 345                 350

Val Lys Met Gln Val Ala Glu Asp Gly Phe Ile Gln Asn Gly Pro Glu
        355                 360                 365

Glu Glu Ile Val Val Gly Val Ile Asp Pro Ser Glu Asn Ile Gln Glu
    370                 375                 380

Ile Asn Thr Ala Ile Ser Asp Asn Tyr Thr Tyr Asn Ile Pro Gly Ile
385                 390                 395                 400

Val Asn Asn Asn Pro Phe Tyr Ile Leu Phe Thr Val Asn Thr Thr Gly
                405                 410                 415

Ile Tyr Lys Ile Asn Ala Gln Asn Asn Leu Pro Ser Leu Lys Ile Tyr
            420                 425                 430

Glu Ala Ile Gly Ser Gly Asn Arg Asn Phe Gln Ser Gly Asn Leu Cys
        435                 440                 445

Asp Asp Asp Ile Lys Ala Ile Asn Tyr Ile Thr Gly Phe Asp Ser Pro
    450                 455                 460

Asn Ala Lys Ser Tyr Leu Val Val Leu Leu Asn Lys Asp Lys Asn Tyr
465                 470                 475                 480

Tyr Ile Arg Val Pro Gln Thr Ser Ser Asn Ile Glu Asn Gln Ile Gln
                485                 490                 495

Phe Lys Arg Glu Glu Gly Asp Leu Arg Asn Leu Met Asn Ser Ser Val
            500                 505                 510

Asn Ile Ile Asp Asn Leu Asn Ser Thr Gly Ala His Tyr Tyr Thr Arg
        515                 520                 525

Gln Ser Pro Asp Val His Asp Tyr Ile Ser Tyr Glu Phe Thr Ile Pro
    530                 535                 540

Gly Asn Phe Asn Asn Lys Asp Thr Ser Asn Ile Arg Leu Tyr Thr Ser
545                 550                 555                 560

Tyr Asn Gln Gly Ile Gly Thr Leu Phe Arg Val Thr Glu Thr Ile Asp
                565                 570                 575

Gly Tyr Asn Leu Ile Asn Ile Gln Gln Asn Leu His Leu Leu Asn Asn
            580                 585                 590

Thr Asn Ser Ile Arg Leu Leu Asn Gly Ala Ile Tyr Ile Leu Lys Val
        595                 600                 605

Glu Val Thr Glu Leu Asn Asn Tyr Asn Ile Arg Leu His Ile Asp Ile
    610                 615                 620

Thr Asn
625
```

MUTANT HEMAGGLUTININ COMPLEX PROTEIN, AND METHOD FOR CULTURING PLURIPOTENT STEM CELLS USING SAME

SEQUENCE LISTING SUBMISSION VIA EFS-WEB

A computer readable text file, entitled "SequenceListing.txt," created on or about Dec. 22, 2016 with a file size of about 34 kb contains the sequence listing for this application and is hereby incorporated by reference in its entirety.

TECHNICAL FIELD

The present disclosure relates to a mutant hemagglutinin complex protein derived from *Clostridium botulinum* type B, a method for culturing stem cells having pluripotency, a method for removing cells deviated from the undifferentiated state, the cells being cells that have emerged or may possibly emerge during culture of stem cells having pluripotency, a method for maintaining an undifferentiated state of stem cells having pluripotency, a method for culturing iPS cells, a method for dividing a cell cluster of iPS cells, and a kit to be used for these methods.

BACKGROUND ART

In mass culture of pluripotent stem cells such as human iPS (induced pluripotent stem) cells, a series of amplification culture (subculture) processes are repeated so that many undifferentiated cells are prepared. It is known that in this series of culture processes, cells deviated from the undifferentiated state, that is, "deviated cells", spontaneously emerge.

It is known that the deviated cells have a division potential that is nearly equivalent to that of undifferentiated cells, and induce the conversion from undifferentiated cells to deviated cells. In other words, when deviated cells emerge, the proliferation rate thereof exceeds that of undifferentiated cells, and the proliferation of undifferentiated cells is suppressed.

The emergence of deviated cells is frequently observed in culturing operations performed by unskilled culture operators. Furthermore, an excessively large colony size and fusion of colonies are known to be factors of the emergence. Therefore, subculture at low confluence and maintenance of uniformity at seeding can reduce the frequency of emergence of deviated cells to some extent. Moreover, by using a medium developed in recent years, the frequency of emergence of deviated cells is suppressed to some extent. Deviated cells, however, still spontaneously emerge, and in the case where the cells emerge, it is still essential to remove colonies that contain deviated cells.

In order to maintain the undifferentiated state, colonies containing deviated cells are carefully removed by pipetting operations under a microscope apparatus upon subculture. A device performing such an operation of removing colonies, for example, an observing device combined with pipetting performed by robot handling, has been developed as well.

Furthermore, Patent Document 1 discloses culture of pluripotent stem cells in the presence of activin for proliferating pluripotent stem cells such as iPS cells while maintaining undifferentiated states thereof.

PRIOR ART DOCUMENTS

Patent Document

[Patent Document 1] JP2012-143229A

SUMMARY OF THE INVENTION

Problem to be Solved by the Invention

As described above, a deviation phenomenon tends to occur in subculture of pluripotent stem cells such as human iPS cells, and maintaining the undifferentiated state is difficult. After several times of subculture, it is likely that the deviation phenomenon occurs in many iPS cell colonies and the colonies can become colonies that contain cells deviated from the undifferentiated state. Complicated operations such as careful culturing and careful colony sorting are therefore indispensable. From the viewpoint of promoting the stem cell industry as well, a method for maintaining undifferentiated states of pluripotent stem cells, which involves less complicated operations and can be performed by a non-expert, has been desired.

Furthermore, with respect to pluripotent stem cells such as human iPS cells, in terms of practical applications thereof to regenerative medicine and drug discovery research, a reliable supply of a large amount of high-quality cells has been desired. Recently, therefore, suspension culture has been attempted but there are problems that, for example, cells are damaged when a cell cluster is divided. Therefore, there has been a demand for a method that enables a large amount of pluripotent stem cells such as human iPS cells to be cultured easily and efficiently.

Hemagglutinin (HA) derived from *Clostridium botulinum* is a component of a botulinum neurotoxin complex. Recently, it has been discovered that the HA has a molecular mechanism in which the HA specifically binds to E-cadherin that is a cell adhesion molecule, and thereby breaks down the barrier between intestinal epithelial cells. The present inventors have been attempting to remove "cells deviated from the undifferentiated state," which emerge in colonies during the culture of stem cells having pluripotency, using the molecular mechanism of the HA.

The present disclosure, in one aspect, provides a novel hemagglutinin that can remove "a cell deviated from the undifferentiated state", which emerges in a colony during culture of stem cells having pluripotency.

The present disclosure, in one aspect, provides a novel method for culturing stem cells having pluripotency using hemagglutinin.

Means for Solving Problem

The present disclosure, in one aspect, relates to a mutant hemagglutinin complex protein derived from *Clostridium botulinum* type B, the complex protein containing at least subcomponents HA2 and HA3 of hemagglutinin derived from *Clostridium botulinum* type B, and amino acids constituting a glycosylation site, with at least one of the amino acids having been mutated.

The present disclosure, in one aspect, relates to a mutant hemagglutinin complex protein derived from *Clostridium botulinum* type B, the complex protein consisting of subcomponents HA1, HA2, and HA3, and one or two amino acids selected from an amino acid corresponding to asparagine at position 264 in a wild-type amino acid sequence of the subcomponent HA1, an amino acid corresponding to asparagine at position 286 in the wild-type amino acid sequence of the subcomponent HA1, and an amino acid corresponding to arginine at position 528 in a wild-type amino acid sequence of the subcomponent HA3 having been mutated.

The present disclosure, in one aspect, relates to a method for culturing stem cells having pluripotency, the method including culturing the stem cell having pluripotency in the presence of a mutant hemagglutinin complex protein of the present disclosure.

The present disclosure, in one aspect, relates to a method for removing a cell deviated from the undifferentiated state, the cell being a cell that has emerged or may possibly emerge during culture of stem cells having pluripotency, the method including culturing the stem cell having pluripotency in the presence of a mutant hemagglutinin complex protein of the present disclosure.

The present disclosure, in one aspect, relates to a method for culturing iPS cells of human origin, the method including culturing the iPS cells in suspension culture in the presence of hemagglutinin derived from *Clostridium botulinum.*

The present disclosure, in one aspect, relates to a method for dividing a cluster of iPS cells of human origin, the method including culturing the iPS cells in suspension culture in the presence of hemagglutinin derived from *Clostridium botulinum.*

Effects of the Invention

The present disclosure, in one aspect, can provide an effect that "a cell deviated from the undifferentiated state", which emerges in a colony during culture of stem cells having pluripotency, can be removed.

The present disclosure, in one aspect, can provide an effect that stem cells having pluripotency can be cultured easily and efficiently in large quantities.

DESCRIPTION OF PREFERRED EMBODIMENTS

Figure 1:
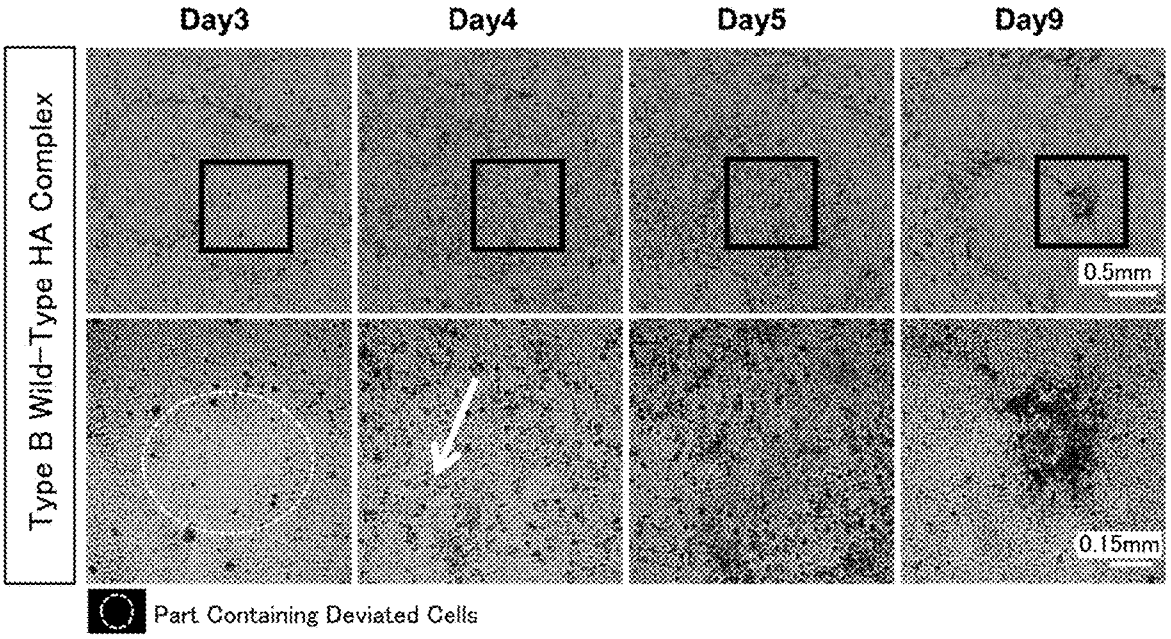
FIG. 1 shows exemplary micrographs of iPS cell colonies in the case where a type B wild-type HA complex was added at day 3 (Example 2).

Wild-type hemagglutinin derived from *Clostridium botulinum* is known to be a complex consisting of three subcomponents, HA1 (33K, HA-33), HA2 (17K, HA-17), and HA3 (70K, HA-70). Particularly, wild-type hemagglutinin derived from *Clostridium botulinum* type B is a dodecamer complex consisting of subcomponents HA1, HA2, and HA3 at a ratio of 2:1:1. Furthermore, the wild-type hemagglutinin derived from *Clostridium botulinum* type B is known to bind to E-cadherin to inhibit cell-cell adhesion caused by the E-cadherin and is known to provide E-cadherin binding activity even in the case of a complex of HA2 and HA3.

The present disclosure, in one aspect, is based on knowledge that as long as hemagglutinin contains at least subcomponents HA2 and HA3 of hemagglutinin derived from *Clostridium botulinum* type B, an amino acid sequence constituting an E-cadherin binding site, and amino acids constituting a carbohydrate recognition domain (glycosylation site), with at least one of the amino acids having been mutated (mutant hemagglutinin), it can selectively inhibit cell-cell adhesion of cells deviated from the undifferentiated state (hereinafter also referred to as "deviated cells"), which have emerged and/or emerge in colonies during culture of stem cells having pluripotency, and further can selectively remove deviated cells.

Furthermore, the present disclosure, in one aspect, is based on knowledge that when stem cells having pluripotency are subjected to suspension culture in the presence of hemagglutinin derived from *Clostridium botulinum*, even in the case of delicate cells like human iPS cells, a cell cluster can be divided into blobs easily and efficiently and furthermore, a new cell cluster can be formed from the blobs.

Furthermore, the present disclosure, in one aspect, is based on knowledge that hemagglutinin (type A mutant hemagglutinin) that contains at least subcomponents HA2 and HA3 of hemagglutinin derived from *Clostridium botulinum* type A, an amino acid sequence constituting an E-cadherin binding site, and amino acids constituting a carbohydrate recognition domain, with at least one of the amino acids having been mutated, can remove deviated cells efficiently as compared to the type B wild-type hemagglutinin.

[Stem Cells Having Pluripotency]

In the present disclosure, the stem cell having pluripotency is a human pluripotent stem cell, in one or more non-limiting embodiments. In the present disclosure, the human pluripotent stem cell is a human iPS (induced pluripotent stem) cell or a human ES (embryonic stem) cell, in one or more non-limiting embodiments.

[Cells Deviated from the Undifferentiated State (Deviated Cells)]

In the present disclosure, the cells deviated from the undifferentiated state (deviated cells) are different in morphology from cells in the undifferentiated state and therefore can be distinguished, in one or more non-limiting embodiments. It is possible to confirm that a cell has become a deviated cell, by the disappearance of an undifferentiation marker, in one or more non-limiting embodiments. The undifferentiation marker is Oct3/4, Nanog, SSEA-4, or TRA-1-60 in one or more non-limiting embodiments.

[Mutant Hemagglutinin (HA) Complex Protein]

The present disclosure relates to a mutant hemagglutinin complex protein derived from *Clostridium botulinum* type B (hereinafter also referred to as a "mutant HA complex protein of the present disclosure"), in one or more embodiments. The mutant HA complex protein of the present disclosure is a mutant hemagglutinin complex protein that contains at least subcomponents HA2 and HA3 of hemagglutinin derived from *Clostridium botulinum* type B and amino acids constituting a glycosylation site, with at least one of the amino acids having been mutated. The mutant HA complex protein of the present disclosure is a mutant hemagglutinin complex protein that has an amino acid sequence constituting an E-cadherin binding site and contains amino acids constituting a glycosylation site, with at least one of the amino acids having been mutated, in one or more embodiments. Furthermore, the mutant HA complex protein of the present disclosure is a mutant hemagglutinin complex protein that has E-cadherin binding activity and contains amino acids constituting a glycosylation site, with at least one of the amino acids having been mutated, in one or more embodiments. Moreover, the mutant HA complex protein of the present disclosure is a mutant hemagglutinin complex protein that has E-cadherin function inhibitory activity and contains amino acids constituting a glycosylation site, with at least one of the amino acids having been mutated, in one or more embodiments.

The mutant HA complex protein of the present disclosure can provide an effect that cell-cell adhesion of deviated cells that have emerged and/or emerge in colonies during culturing stem cells having pluripotency can be inhibited, in one or more embodiments. The mutant HA complex protein of the present disclosure can provide effects that preferably deviated cells can be removed from colonies, and the colonies that are formed during culture of stem cells having pluripotency can be maintained in an undifferentiated state (the colonies consisting of stem cells having pluripotency that are maintained in an undifferentiated state can continue to be formed).

The mutant HA complex protein of the present disclosure contains at least subcomponents HA2 and HA3 of hemagglutinin derived from *Clostridium botulinum* type B and, in one or more embodiments, may further contain a subcomponent HA1. In one or more embodiments, the mutant HA complex protein of the present disclosure is a complex consisting of two components, HA2 and HA3, and from the viewpoint that cell-cell adhesion can be inhibited further efficiently and deviated cells can be removed further efficiently, it is a complex consisting of three components, HA1, HA2, and HA3.

In the mutant HA complex protein of the present disclosure, at least one of the amino acids constituting a glycosylation site has been mutated. In one or more embodiments, the mutant HA complex protein of the present disclosure can also be referred to as a mutant hemagglutinin complex protein in which at least part or all of the glycosylation activity of wild-type hemagglutinin derived from *Clostridium botulinum* type B has been deleted. As amino acids constituting the glycosylation site in wild-type hemagglutinin derived from *Clostridium botulinum* type B, the present inventors have found, for example, asparagine at position 286 in the amino acid sequence (SEQ ID NO: 1) of HA1 and arginine at position 528 in the amino acid sequence (SEQ ID NO: 3) of HA3. Furthermore, examples of other known amino acids include asparagine at position 264 in the amino acid sequence (SEQ ID NO: 1) of HA1 (for example, KwangKook Lee et al, Biochem Biophys Res Commun 2014 Apr. 4, Vol 446, Issue 2, pp. 568-573). In the mutant HA complex protein of the present disclosure, in one or more embodiments, these amino acids or amino acids corresponding to these amino acids have been mutated, and from the viewpoint that deviated cells can be efficiently removed from colonies, preferably arginine at position 528 in the amino acid sequence (SEQ ID NO: 3) of HA3 or an amino acid corresponding thereto has been mutated, and more preferably, arginine at position 528 in the amino acid sequence (SEQ ID NO: 3) of HA3 or an amino acid corresponding thereto and asparagine at position 286 in the amino acid sequence (SEQ ID NO: 1) of HA1 or an amino acid corresponding thereto have been mutated. In the present disclosure, "amino acids corresponding to these amino acids" denote amino acids located at conformationally equivalent positions to those of wild-type amino acids constituting the above-mentioned glycosylation site. In the present disclosure, in one or more embodiments, mutation of amino acids includes substitution with amino acids that do not recognize a carbohydrate chain, preferably substitution with alanine.

The mutant HA complex protein of the present disclosure has an amino acid sequence constituting an E-cadherin binding site in wild-type hemagglutinin derived from *Clostridium botulinum* type B. That is, in one or more embodiments, the mutant HA complex protein of the present disclosure has E-cadherin binding activity. Therefore, the present disclosure, in another aspect, relates to a mutant hemagglutinin complex protein derived from *Clostridium botulinum* type B that contains at least subcomponents HA2 and HA3 of hemagglutinin derived from *Clostridium botulinum* type B, has E-cadherin binding activity, and contains amino acids constituting a glycosylation site, with at least one of the amino acids having been mutated. As the E-cadherin binding site, an E-cadherin binding site in wild-type hemagglutinin derived from *Clostridium botulinum* type A having E-cadherin binding activity in the wild-type hemagglutinin derived from *Clostridium botulinum* type B has been analyzed (for example, KwangKook Lee et al, Science 2014 Jun. 20, Vol. 344, no. 6190 pp. 1405-1410).

In one or more embodiments, the mutant HA complex protein of the present disclosure contains, as the subcomponent HA3, part or all of the amino acid sequence in which arginine at position 528 or an amino acid corresponding thereto has been mutated in the amino acid sequence (SEQ ID NO: 3) of a wild type of HA3 (wild-type HA3).

In one or more embodiments, the mutant HA complex protein of the present disclosure contains, as the subcomponent HA2, part or all of the amino acid sequence (SEQ ID NO: 2) of a wild type of HA2 (wild-type HA2).

In one or more embodiments, the mutant HA complex protein of the present disclosure contains, as the subcomponent HA1, part or all of the amino acid sequence in which asparagine at position 264 or an amino acid corresponding thereto and/or asparagine at position 286 or an amino acid corresponding thereto have/has been mutated in the amino acid sequence (SEQ ID NO: 1) of a wild type of HA1 (wild-type HA1).

In one or more embodiments, the mutant HA complex protein of the present disclosure is a mutant hemagglutinin complex protein that consists of subcomponents HA1, HA2, and HA3, with one or both of an amino acid corresponding to asparagine at position 286 in an amino acid sequence of a wild type of the subcomponent HA1 and an amino acid corresponding to arginine at position 528 in an amino acid sequence of a wild type of the subcomponent HA3 having been mutated.

Examples of a first embodiment of the mutant HA complex protein of the present disclosure include a mutant HA complex (a mutant HA complex 1) containing HA1 in which asparagine at position 264 and/or asparagine at position 286 have/has been mutated in the amino acid sequence (SEQ ID NO: 1) of wild-type HA1 (mutant HA1), wild-type HA2, and wild-type HA3. In one or more embodiments of the mutant HA complex 1, it is acceptable as long as at least one of the subcomponents HA1 contained in the mutant HA complex 1 is mutant HA1, and it is preferable that all HA1 be mutant HA1.

Examples of a second embodiment of the mutant HA complex protein of the present disclosure include a mutant HA complex (a mutant HA complex 2) containing wild-type HA1, wild-type HA2, and HA3 in which arginine at position 528 or an amino acid corresponding thereto has been mutated in the amino acid sequence (SEQ ID NO: 3) of wild-type HA3 (mutant HA3). In one or more embodiments of the mutant HA complex 2, it is acceptable as long as at least one of the subcomponents HA3 contained in the mutant HA complex 2 is mutant HA3, and it is preferable that all HA3 be mutant HA3.

Examples of a third embodiment of the mutant HA complex protein of the present disclosure include a mutant HA complex (a mutant HA complex 3) containing mutant HA1, wild-type HA2, and mutant HA3, and preferably containing HA1 (SEQ ID NO: 4) in which asparagine at position 286 in the amino acid sequence (SEQ ID NO: 1) of wild-type HA1 has been mutated to alanine, wild-type HA2 (SEQ ID NO: 2), and HA3 (SEQ ID NO: 5) in which arginine at position 528 in the amino acid sequence (SEQ ID NO: 3) of wild-type HA3 has been mutated to alanine, from the viewpoint of further efficiently inhibiting cell-cell adhesion and further efficiently removing deviated cells. In one or more embodiments of the mutant HA complex 3, it is acceptable as long as at least one of the subcomponents HA1 contained in the mutant HA complex 3 is mutant HA1, and it is preferable that all HA1 be mutant HA1. Furthermore, it is acceptable as long as at least one of the subcomponents HA3 contained in the mutant HA complex 3 is mutant HA3, and it is preferable that all HA3 be mutant HA3.

In one or more embodiments, the mutant complex protein of the present disclosure may include a tag binding to the C-terminal of the subcomponent HA1. In one or more embodiments, examples of the tag that binds to the C-terminal include a FLAG-tag and a D4-tag (DDDD, SEQ ID NO: 15). In the mutant complex protein of the present disclosure, in one or more embodiments, the N-terminal of the subcomponent HA1 preferably has no tag binding thereto and the N-terminal of the subcomponent HA1 preferably has no His-tag or FLAG-tag binding thereto.

[Method for Culturing Stem Cells Having Pluripotency]

The present disclosure, in one aspect, is a method for culturing stem cells having pluripotency, the method including performing cell culture in the presence of a mutant HA complex protein of the present disclosure (hereinafter also referred to as "the culturing method of the present disclosure"). According to the culturing method of the present disclosure, since cell culture is performed in the presence of a mutant HA complex protein of the present disclosure, the method can provide effects that deviated cells can be removed and the colonies formed during culture of the stem cells having pluripotency can be maintained in an undifferentiated state, in one or more embodiments. Furthermore, according to the culturing method of the present disclosure, since cell culture is performed in the presence of a mutant HA complex protein of the present disclosure, a spheroid cell cluster can be divided efficiently even in the case of delicate cells such as iPS cells of human origin, and preferably stem cells having pluripotency can be efficiently cultured in large quantities, in one or more embodiments. In the culturing method of the present disclosure, examples of the cell culture include adhesion culture (plate culture) and suspension culture, in one or more embodiments.

<Adhesion Culture>

Examples of a first embodiment of the culturing method of the present disclosure include performing cell culture by adhesion culture. In one or more embodiments, when adhesion culture is employed as the cell culture, an effect can be achieved that deviated cells can be removed from the colonies formed on the culture surface. In another aspect, therefore, the present disclosure relates to a method for removing cells deviated from an undifferentiated state, the cells being cells that have emerged or may possibly emerge during culture of stem cells having pluripotency, the method including performing cell culture in the presence of a mutant hemagglutinin complex protein of the present disclosure. Furthermore, in another aspect, the present disclosure relates to a method for forming a colony consisting of cells in an undifferentiated state out of a colony where cells deviated from the undifferentiated state have emerged, the method including culturing the colony where cells deviated from the undifferentiated state have emerged, in the presence of a mutant HA complex protein of the present disclosure. In another aspect, the present disclosure relates to a method for maintaining the undifferentiated state of stem cells having pluripotency, the method including performing cell culture in the presence of a mutant HA complex protein of the present disclosure.

In one or more embodiments, the culturing method, the removing method, the colony forming method, and/or the maintaining method of the present disclosure can efficiently remove deviated cells from a colony and can efficiently culture undifferentiated cells alone. In one or more embodiments, the culturing method and the removing method of the present disclosure can remove deviated cells while maintaining a closed space during the culture performed with a culture device, and can perform colony selection that allows the cells composing a colony to be substantially undifferentiated cells alone.

The cell culture in the first embodiment can use culture conditions, a culture medium, and the like, which are conventionally used and/or will be developed in the future for stem cells having pluripotency, and it can be performed by allowing the mutant HA complex protein of the present disclosure to be present in the medium under said culture conditions. In one or more non-limiting embodiments, the mutant HA complex protein of the present disclosure may be added to a culture medium under culture, or alternatively, a medium, to which the mutant HA complex protein of the present disclosure has been added beforehand, may be used for culture. In one or more non-limiting embodiments, the mutant HA complex protein of the present disclosure may be added as required when the emergence of deviated cells is observed in a colony. As the culture medium, the culture plate, and the like, those commercially available may be used.

In one or more embodiments, from the viewpoint of efficiently removing deviated cells, the mutant HA complex protein of the present disclosure used in the culturing method, the removing method, the colony forming method, and/or the maintaining method of the present disclosure preferably contains mutant HA3 and more preferably contains mutant HA1 and mutant HA3. In one or more non-limiting embodiments, from the viewpoint of efficiently removing undifferentiated cells, the concentration of the mutant HA complex protein of the present disclosure present in the medium is, for example, 5 nM or more, 10 nM or more, or alternatively, 15 nM or more. From the same viewpoint, the concentration is 200 nM or less, 150 nM or less, or alternatively, 100 nM or less In the culturing method, the removing method, the colony forming method and/or the maintaining method of the present disclosure, the mutant HA complex protein added into the medium can be spontaneously removed by intracellular absorption (for example, endocytosis), in one or more embodiments. Alternatively, an adsorption column that uses a tag attached to the mutant HA complex protein as the target is provided and a medium is circulated, and thereby the mutant HA complex protein may be forcibly recovered from the medium. In this manner, the mutant HA complex protein is spontaneously and/or forcibly removed/recovered and thereby deviated cells can be timely removed temporarily or continuously. In one or more embodiments, the culturing method of the present disclosure includes performing cell culture of stem cells having pluripotency by automatic operation using a bioreactor.

In one or more non-limiting embodiments, the cell culture of the first embodiment may be culture using feeder cells or may be feeder-free culture. In one or more non-limiting embodiments, examples of the feeder cells include MEF (Mouse Embryo Fibroblast) cells, SL10, and SNL 76/7 feeder cells. Among the feeder cells, those that allow the migration speed of stem cells having pluripotency to be relatively slow are preferred in one or more non-limiting embodiments. In one or more non-limiting embodiments, the feeder cells are preferably SNL 76/7 feeder cells, from the viewpoint that the migration of stem cells having pluripotency is relatively slow and a colony of deviated cells is allowed to emerge in the center part of a colony during culture of stem cells having pluripotency.

<Suspension Culture>

Examples of a second embodiment of the culturing method of the present disclosure include performing cell culture by suspension culture. In one or more embodiments, when suspension culture is employed as the cell culture, a cell cluster can be efficiently divided even in the case of delicate cells such as iPS cells of human origin, and preferably stem cells having pluripotency can be efficiently cultured in large quantities. Therefore, the present disclosure, in another aspect, relates to a method for dividing a cell cluster of stem cells having pluripotency, the method including performing suspension culture of the stem cells having pluripotency in the presence of a mutant HA complex protein of the present disclosure.

In one or more embodiments, the culturing method of the second embodiment includes performing suspension culture of the cell cluster of stem cells in the presence of hemagglutinin derived from *Clostridium botulinum* to divide the cell cluster of stem cells into blobs, and performing suspension culture of the blobs to form a new cell duster. In one or more embodiments, in the culturing method of the second embodiment, a cell cluster is formed in the same medium as that used for dividing the cell duster. In one or more embodiments, the mutant HA complex protein of the present disclosure added into the medium can be spontaneously removed by intracellular absorption (for example, endocytosis). In one or more embodiments, therefore, the culturing method of the second embodiment can divide a cell cluster and form a new cell cluster by continuous culture without washing the mutant HA complex protein. In one or more embodiments, the culturing method of the second embodiment does not include a process of washing the mutant HA complex protein. Furthermore, in one or more embodiments, an adsorption column that uses a tag attached to the mutant HA complex protein of the present disclosure as the target is provided and a medium is circulated, and thereby the substance may be forcibly recovered from the medium. In one or more embodiments, the culturing method of the present disclosure, in which as described above, the mutant HA complex protein can be spontaneously and/or forcibly removed/recovered and thereby the division of the cell cluster is controlled to allow the division effect to be timely exhibited temporarily or continuously, includes performing cell culture of stem cells having pluripotency by automatic operation using a bioreactor.

The cell culture in the second embodiment can use culture conditions, a culture medium, and the like, which have been conventionally used and/or are to be developed in the future, for stem cells having pluripotency, and it can be achieved by allowing the mutant HA complex protein of the present disclosure to be present in the medium under said culture conditions. In one or more non-limiting embodiments, the mutant HA complex protein of the present disclosure may be added to the culture medium under culture, or alternatively, a medium, to which the mutant HA complex protein of the present disclosure has been added beforehand, may be used for culture. For the culture medium, the culture vessel, and the like, those which are commercially available may be used.

In one or more non-limiting embodiments, from the viewpoint of efficiently removing undifferentiated cells, the concentration of the mutant HA complex protein of the present disclosure present in the medium is, for example, 5 nM or more, 10 nM or more, or alternatively, 15 nM or more. From the same viewpoint, the concentration is 200 nM or less, 150 nM or less, or alternatively, 100 nM or less.

In one or more embodiments, the suspension culture can use culture conditions, a culture medium, and the like, which have been conventionally used and/or are to be developed in the future, for stem cells having pluripotency, and it can be achieved by allowing the mutant HA complex protein of the present disclosure to be present in the medium under said culture conditions.

[Method for Culturing iPS Cells]

In one or more embodiments, the present disclosure relates to a method for culturing iPS cells, the method including performing suspension culture of the iPS cells in the presence of hemagglutinin derived from *Clostridium botulinum* (hereinafter also referred to as "the method for culturing iPS cells of the present disclosure"). According to the method for culturing iPS cells of the present disclosure, since a spheroid cell cluster can be efficiently divided even in the case of delicate cells such as iPS cells of human origin, the iPS cells can be efficiently cultured in large quantities. In one or more embodiments, therefore, the present disclosure relates to a method for dividing a cell cluster of iPS cells, the method including performing suspension culture of iPS stem cells in the presence of hemagglutinin derived from *Clostridium botulinum* (hereinafter also referred to as "the dividing method of the present disclosure").

In one or more embodiments, the method for culturing iPS cells of the present disclosure includes performing suspension culture of a cell cluster of iPS cells in the presence of hemagglutinin derived from *Clostridium botulinum* to divide the cell cluster of iPS cells into blobs, and performing suspension culture of the blobs to form a new cell duster. In one or more embodiments, in the method for culturing iPS cells of the present disclosure, a cell cluster is formed in the same medium as that used for dividing the cell duster. In one or more embodiments, the mutant HA complex protein of the present disclosure added into the medium can be spontaneously removed by intracellular absorption (for example, endocytosis). In one or more embodiments, therefore, the method for culturing iPS cells of the present disclosure can divide a cell cluster and form a new cell cluster by continuous culture without washing the mutant HA complex protein. In one or more embodiments, the method for culturing iPS cells of the present disclosure does not include a process of washing the mutant HA complex protein. Furthermore, in one or more embodiments, an adsorption column that uses a tag attached to the mutant HA complex protein of the present disclosure as the target is provided and a medium is circulated, and thereby the substance may be forcibly recovered from the medium. In one or more embodiments, the culturing method of the present disclosure, in which as described above, the mutant HA complex protein can be spontaneously and/or forcibly removed/recovered and thereby the division of the cell cluster is controlled to allow the division effect to be timely exhibited temporarily or continuously, includes performing cell culture of stem cells having pluripotency by automatic operation using a bioreactor.

Examples of the hemagglutinin derived from *Clostridium botulinum* that is used in the method for culturing iPS cells and the dividing method of the present disclosure include, as one or more embodiments, hemagglutinin derived from *Clostridium botulinum* type A and hemagglutinin derived from *Clostridium botulinum* type B. In one or more embodiments, the hemagglutinin derived from *Clostridium botulinum* type B preferably contains a subcomponent HA1 with a tag binding to the C-terminal. In one or more embodiments, examples of the hemagglutinin derived from *Clostridium botulinum* type B include a mutant HA complex protein of the present disclosure.

In the method for culturing iPS cells and the dividing method of the present disclosure, the hemagglutinin derived from *Clostridium botulinum* type Ais preferred from the viewpoint that a cell cluster can be efficiently divided at low concentration. In one or more embodiments, examples of the hemagglutinin derived from *Clostridium botulinum* type A include hemagglutinin derived from wild-type *Clostridium botulinum* type A and hemagglutinin derived from mutant *Clostridium botulinum* type A to be described later.

In the method for culturing iPS cells and the dividing method of the present disclosure, the conditions for suspension culture, the conditions for adding HA, and the like can be the same as in the case of the culturing method of the second embodiment.

[Composition]

The present disclosure, in another aspect, relates to a composition that contains hemagglutinin derived from *Clostridium botulinum* (hereinafter also referred to as a "composition of the present disclosure"). The composition of the present disclosure can be used for the culturing method of the present disclosure, the removing method of the present disclosure, the colony forming method of the present disclosure, the maintaining method of the present disclosure, and/or the dividing method of the present disclosure. Therefore, the present disclosure, in another aspect, relates to a composition used in the culturing method of the present disclosure, the removing method of the present disclosure, the colony forming method of the present disclosure, the maintaining method of the present disclosure, and/or the dividing method of the present disclosure, the composition containing hemagglutinin derived from *Clostridium botulinum*. Furthermore, the present disclosure, in another aspect, relates to the use of hemagglutinin derived from tulinus in the culturing method of the present disclosure, the removing method of the present disclosure, the colony forming method of the present disclosure, the maintaining method of the present disclosure, and/or the dividing method of the present disclosure. In one or more embodiments, examples of the hemagglutinin derived from *Clostridium botulinum* include the above-mentioned hem agglutinin derived from *Clostridium botulinum* type A and hemagglutinin derived from *Clostridium botulinum* type B as well as complexes thereof. In one or more embodiments, examples of the hemagglutinin derived from *Clostridium botulinum* type B include a mutant HA complex of the present disclosure and a wild-type HA complex.

[Kit]

The present disclosure, in another aspect, relates to a kit including: a medium component for stem cells having pluripotency; and a mutant hemagglutinin complex protein of the present disclosure (hereinafter also referred to as a "kit of the present disclosure"). The "mutant hemagglutinin complex protein" in the kit of the present disclosure is as described above. The kit of the present disclosure can be used for the culturing method, the removing method, the colony forming method, and/or the maintaining method of the present disclosure. The medium component for stem cells having pluripotency is not particularly limited, and a medium component that has been conventionally used or that is to be developed in the future can be used.

[Composition Used for Culturing Stem Cells Having Pluripotency]

The present disclosure, in another aspect, relates to a composition that contains a mutant hemagglutinin complex protein derived from *Clostridium botulinum* and is used for culturing stem cells having pluripotency (hereinafter referred to as a "culture composition of the present disclosure"). The culture composition of the present disclosure can be used for the culturing method of the present disclosure, the removing method of the present disclosure, the colony forming method of the present disclosure, the maintaining method of the present disclosure, and/or the dividing method of the present disclosure.

The mutant hemagglutinin complex protein derived from *Clostridium botulinum* contained in the culture composition of the present disclosure is a mutant hemagglutinin complex protein that contains at least subcomponents HA2 and HA3 of hemagglutinin derived from *Clostridium botulinum*, an amino acid sequence constituting an E-cadherin binding site, and amino acids constituting a glycosylation site, with at least one of the amino acids having been mutated. In the hemagglutinin composing the mutant hemagglutinin complex protein, the type of the *Clostridium botulinum* thereof is not particularly limited as long as it is hemagglutinin that has an interaction with E-cadherin. In one or more embodiments that are not particularly limited, examples of the *Clostridium botulinum* include *Clostridium botulinum* type A and *Clostridium botulinum* type B.

In one or more embodiments, examples of the mutant hemagglutinin complex protein derived from *Clostridium botulinum* include a mutant HA complex protein of the present disclosure, which is a mutant hemagglutinin complex protein derived from *Clostridium botulinum* type B.

In one or more embodiments, examples of the mutant hemagglutinin complex protein derived from *Clostridium botulinum* include a mutant hemagglutinin complex protein derived from *Clostridium botulinum* type A (hereinafter also referred to as a "type A mutant HA complex").

In one or more embodiments, examples of the type A mutant HA complex include a known type A mutant HA complex, in which at least one of the amino acids constituting a glycosylation site has been mutated. Examples of the amino acids constituting a glycosylation site in wild-type hemagglutinin derived from *Clostridium botulinum* type A include asparagine at position 285 in the amino acid sequence (SEQ ID NO: 16) of HA1, as well as arginine at position 528 in the amino acid sequence (SEQ ID NO: 18) of HA3 and asparagine at position 263 in the amino acid sequence (SEQ ID NO: 16) of HA1.

The type A mutant HA complex contains at least subcomponents HA2 and HA3 of the hemagglutinin derived from *Clostridium botulinum* type A and may further contain a subcomponent HA1 in one or more embodiments. In one or more embodiments, the type A mutant HA complex is a complex consisting of two components, HA2 and HA3, and from the viewpoint that cell-cell adhesion can be inhibited more efficiently and deviated cells can be removed more efficiently, it is a complex consisting of three components, HA1, HA2, and HA3.

In the type A mutant HA complex, at least one of the amino acids constituting a glycosylation site has been mutated. In one or more embodiments, the type A mutant HA complex can also be referred to as a mutant hemagglutinin complex protein in which at least part or all of the glycosylation activity of wild-type hemagglutinin derived from *Clostridium botulinum* type A has been deleted. In one or more embodiments, in the type A mutant HA complex, amino acids constituting a glycosylation site or amino acids corresponding thereto have been mutated, and from the viewpoint that deviated cells can be efficiently removed from a colony, preferably arginine at position 528 in the amino acid sequence (SEQ ID NO: 18) of HA3 or an amino acid corresponding thereto has been mutated, and more preferably arginine at position 528 in the amino acid sequence (SEQ ID NO: 18) of HA3 or an amino acid corresponding thereto and asparagine at position 285 in the amino acid sequence (SEQ ID NO: 16) of HA1 or an amino acid corresponding thereto have been mutated.

The type A mutant HA complex has an amino acid sequence constituting the E-cadherin binding site in wild-type hemagglutinin derived from *Clostridium botulinum* type A. That is, in one or more embodiments, the type A mutant HA complex has E-cadherin binding activity.

In one or more embodiments, the type A mutant HA complex contains, as the subcomponent HA3, part or all of the amino acid sequence in which arginine at position 528 in the amino acid sequence (SEQ ID NO: 18) of a wild type of type A HA3 (wild-type HA3) or an amino acid corresponding thereto has been mutated.

In one or more embodiments, the type A mutant HA complex contains, as the subcomponent HA2, part or all of the amino acid sequence (SEQ ID NO: 17) of a wild type of type A HA2 (wild-type HA2).

In one or more embodiments, the type A mutant HA complex contains, as the subcomponent HA1, part or all of the amino acid sequence in which asparagine at position 264 or an amino acid corresponding thereto and/or asparagine at position 286 or an amino acid corresponding thereto have/has been mutated in the amino acid sequence (SEQ ID NO: 16) of a wild type of type AHA1 (wild-type HA1).

In one or more embodiments, the type A mutant HA complex may has a tag binding to the C-terminal of the subcomponent HA1. In one or more embodiments, examples of the tag binding to the C-terminal include a FLAG-tag and a D4-tag (DDDD, SEQ ID NO: 15). In one or more embodiments, the mutant complex protein of the present disclosure has preferably no tag binding to the N-terminal of the subcomponent HA1 and has preferably no His-tag or FLAG-tag binding to the N-terminal of the subcomponent HA1.

In one or more embodiments, the present disclosure relates to a method for culturing stem cells having pluripotency using a culture composition of the present disclosure, a method for removing a cell deviated from an undifferentiated state, the cell being a cell that has emerged or may possibly emerge during culture of stem cells having pluripotency, a method for maintaining the undifferentiated state of stem cells having pluripotency. In one or more embodiments, these methods include performing cell culture of stem cells having pluripotency in the presence of the culture composition of the present disclosure.

The present disclosure further relates to one or more non-limiting embodiments described below.

<A1> A mutant hemagglutinin complex protein derived from *Clostridium botulinum* type B, the complex protein containing:

at least subcomponents HA2 and HA3 of hemagglutinin derived from *Clostridium botulinum* type B; and at least one of mutation s of amino acids constituting a glycosylation site of hemagglutinin derived from *Clostridium botulinum* type B.

<A2> A mutant hemagglutinin complex protein derived from *Clostridium botulinum* type B, the complex protein containing:

at least subcomponents HA2 and HA3 of hemagglutinin derived from *Clostridium botulinum* type B;

an amino acid sequence constituting an E-cadherin binding site; and at least one of mutations of amino acids constituting a glycosylation site of hemagglutinin derived from *Clostridium botulinum* type B.

<A3> The mutant hemagglutinin complex protein according to <A1>, wherein the complex protein further contains a subcomponent HA1 of hemagglutinin derived from *Clostridium botulinum* type B.

<A4> The mutant hemagglutinin complex protein according to <A3>, wherein the amino acids constituting a glycosylation site are selected from the group consisting of an amino acid corresponding to asparagine at position 264 in an amino acid sequence of a wild type of the HA1, an amino acid corresponding to asparagine at position 286 in the amino acid sequence of a wild type of the HA1, and an amino acid corresponding to arginine at position 528 in an amino acid sequence of a wild type of the HA3.

<A5> A mutant hemagglutinin complex protein derived from *Clostridium botulinum* type B, the complex protein consisting of subcomponents HA1, HA2, and HA3, and the complex protein comprising one or both of mutations of an amino acid corresponding to asparagine at position 286 in an amino acid sequence of a wild type of the subcomponent HA1 and an amino acid corresponding to arginine at position 528 in an amino acid sequence of a wild type of the subcomponent HA3.

<A6> The mutant hemagglutinin complex protein according to any one of <A1> to

<A5>, wherein the subcomponent HA1 is tagged at a C-terminal thereof.

<A8> The mutant hemagglutinin complex protein according to any one of <A1> to

<A7>, wherein the complex protein has E-cadherin function inhibitory activity.

<A9> The mutant hemagglutinin complex protein according to any one of <A1> to

<A8>, wherein the complex protein has E-cadherin binding activity.

<A10> The mutant hemagglutinin complex protein according to any one of <A1> to

<A9>, wherein the complex protein has an amino acid sequence constituting an E-cadherin binding site.

<B1> A method for culturing a stem cell having pluripotency, the method including culturing the stem cell having pluripotency in the presence of a mutant hemagglutinin complex protein according to any one of <A1> to <A10>.

<B2> The method according to <B1>, wherein the culturing is performed by adhesion culture or suspension culture.

<C1> A method for removing a cell deviated from an undifferentiated state, the cell being a cell that has emerged or may possibly emerge during culture of a stem cell having pluripotency, the method including culturing the stem cell having pluripotency in the presence of a mutant hemagglutinin complex protein according to any one of <A1> to <A10>.

<C2> A method for maintaining an undifferentiated state of a stem cell having pluripotency, the method including culturing the stem cell having pluripotency in the presence of a mutant HA complex protein according to any one of <A1> to <A10>.

<D1> A method for culturing iPS cells of human origin, the method including culturing the iPS cells in suspension culture in the presence of hemagglutinin derived from *Clostridium botulinum.*

<D2> The method according to <D1>, wherein the method includes; culturing a cell cluster of the iPS cells in suspension culture in the presence of hemagglutinin derived from *Clostridium botulinum* to divide the cell cluster into blobs; and culturing the blobs to form a new cell cluster in suspension culture, the new cell cluster is formed in the same medium as that in which the cell cluster is divided.

<D3> A method for dividing a cell cluster of iPS cells of human origin, the method including culturing the iPS cells in suspension culture in the presence of hemagglutinin derived from *Clostridium botulinum.*

<D4> The method according to any one of <D1> to <D3>, wherein the hemagglutin derived from *Clostridium botulinum* is taken up by endocytosis.

<D5> The method according to any one of <D1> to <D4>, wherein the hemagglutinin derived from *Clostridium botulinum* is selected from the group consisting of hemagglutinin derived from *Clostridium botulinum* type A and hemagglutinin derived from *Clostridium botulinum* type B.

<D6> The method according to <D5>, wherein the hemagglutinin derived from *Clostridium botulinum* type B contains a mutant hemagglutinin complex protein according to any one of claims 1 to 5.

<E1> A composition containing hemagglutinin derived from *Clostridium botulinum*, the composition being used for a method according to any one of <B1>, <B2>, <C1>, <C2>, and <D1> to <D6>.

<F1> A kit, including a medium component for a stem cell having pluripotency and a mutant hemagglutinin complex protein according to any one of <A1> to <A10>.

<F2> The kit according to <F1>, wherein the kit is used for the method according to any one of <B1>, <B2>, <C1>, <C2>, and <D1> to <D6>.

<G1> A composition containing a mutant hemagglutinin complex protein derived from *Clostridium botulinum*, the complex protein containing;

at least subcomponents HA2 and HA3 of hemagglutinin derived from *Clostridium botulinum;* an amino acid sequence constituting an E-cadherin binding site; and at least one of mutations of amino acids constituting a glycosylation site of hemagglutinin derived from *Clostridium botulinum* type B, and the composition being used for any one of methods selected from the group consisting of:

a method for removing a cell deviated from an undifferentiated state, the cell being a cell that has emerged or may possibly emerge during culture of a stem cell having pluripotency;

a method for maintaining an undifferentiated state of a stem cell having pluripotency;

a method for culturing iPS cells of human origin in suspension culture; and a method for dividing a cell cluster of iPS cells of human origin.

<G2> The composition according to <G1>, wherein the *Clostridium botulinum* is *Clostridium botulinum* type A or *Clostridium botulinum* type B.

<G3> The composition according to <G1> or <G2>, wherein the complex protein further contains a subcomponent HA1 of hemagglutinin derived from *Clostridium botulinum.*

<G4> The composition according to <G3>, wherein the amino acids constituting a glycosylation site is selected from:

the group consisting of an amino acid corresponding to asparagine at position 263 in an amino acid sequence of a wild type of the HA1, an amino acid corresponding to asparagine at position 285 in the amino acid sequence of a wild type of the HA1, and an amino acid corresponding to arginine at position 528 in an amino acid sequence of a wild type of the HA3 in the case of *Clostridium botulinum* type A; and the group consisting of an amino acid corresponding to asparagine at position 264 in the amino acid sequence of a wild type of the HA1, an amino acid corresponding to asparagine at position 286 in the amino acid sequence of a wild type of the HA1, and an amino acid corresponding to arginine at position 528 in the amino acid sequence of a wild type of the HA3 in the case of *Clostridium botulinum* type B.

<H1> A method for culturing a stem cell having pluripotency, the method including culturing the stem cell having pluripotency in the presence of a composition according to any one of <G1> to <G4>.

<H2> The method according to <H1>, wherein the cell culture is adhesion culture or suspension culture.

<H3> A method for removing a cell deviated from an undifferentiated state, the cell being a cell that has emerged or may possibly emerge during culture of a stem cell having pluripotency, the method including culturing the stem cell having pluripotency in the presence of a composition according to any one of <G1> to <G4>.

<H4> A method for maintaining an undifferentiated state of a stem cell having pluripotency, the method including culturing the stem cell having pluripotency in the presence of a composition according to any one of <G1> to <G4>.

EXAMPLES

Hereinafter, the present disclosure is described in further details by way of examples, though these are examples and the present disclosure is not limited by these examples at all.

Example 1

[Production of *Clostridium botulinum* Type B HA Complex]

A wild-type HA complex and mutant HA complexes 1 to 4 derived from *Clostridium botulinum* type B indicated in Table 1 below were produced according to the following procedure. These HA complexes (the wild-type HA complex and the mutant HA complexes) were produced using wild-type HA subcomponents (HA1, HA2, and HA3), mutant HA1 (HA1 N286A, SEQ ID NO: 4), mutant HA3 (HA3 R528A, SEQ ID NO: 5), and mutant HA3X (HA3 K607A, SEQ ID NO: 6) derived from *Clostridium botulinum* type B.

(1) Preparation of Plasmid

With respect to the wild-type, genes that code the following proteins as proteins of the respective HA1, HA2, and HA3 were amplified by PCR using the following primers, respectively, with the genomic DNA of *Clostridium botulinum* B-Okra strain being used as a template.

<Proteins of Respective Subcomponents>

HA1: Recombinant protein with a FLAG-tag binding to the C-terminal of a protein consisting of an amino acid sequence of positions 7 to 294 in the amino acid sequence of SEQ ID NO: 1

HA2: Recombinant protein with a FLAG-tag binding to the N-terminal of a protein consisting of an amino acid sequence of positions 2 to 146 in the amino acid sequence of SEQ ID NO: 2

HA3: Recombinant protein with a Strep-tag binding to the N-terminal of a protein consisting of an amino acid sequence of positions 19 to 626 in the amino acid sequence of SEQ ID NO: 3

<Tag Sequence>

FLAG-tag: DYKDDDDK (SEQ ID NO: 7)

Strep-tag: WSHPQFEK (SEQ ID NO: 8)

<Primer for Amplifying HA1>

HA1 Forward Primer: catgccatgggcatccaaaattcattaaatgac (SEQ ID NO: 9)

HA1 Reverse Primer: cgggatccttacttgtcgtcatcgtctttgtagtctgggttactcatagtccatatc <SEQ ID NO: 10>

<Primer for Amplifying BHA2>

HA2 Forward Primer: tgaataagctttcagctgaaagaacttttc (SEQ ID NO: 11)

HA2 Reverse Primer: cactttggtaccttatatttttcaagtttga (SEQ ID NO: 12)

<Primer for Amplifying HA3>

HA3 Forward Primer: gaaaaagggtaccaatatagtgatactattg (SEQ ID NO: 13)

HA3 Reverse Primer: cgtgtcgacttaattagtaatatctatatgc (SEQ ID NO: 14)

The mutant HA complexes 1 to 4 (Table 1) were produced by a site-directed mutagenesis method using PCR, with a vector containing wild-type HA inserted thereinto being used as a template.

With respect to the DNA fragments that have been amplified, HA1 was inserted into an NcoI-BamHI site of pET52b (+), HA2 was inserted into a HindIII-SalI site of pT7-FLAG-1 (Sigma), and HA3 was inserted into a KpnI-SalI site of pET52b (+) (Novagen) (pET-BHA3).

(2) Protein Expression

The plasmids thus prepared each were independently transformed into *Escherichia coli* strain Rosetta2 (DE3) (Novagen). Protein expression induction was performed using an Overnight Express Autoinduction system 1 (Novagen). The protein expression induction was performed at 30° C. for 36 hours with respect to HA1 and HA3 and at 18° C. for 40 hours with respect to HA2. The *Escherichia coli* was recovered by centrifugation and then was stored at −80° C.

(3) Protein Purification and Production of Complexes

HA1 and HA2 were purified using Anti-FLAG M2 agarose (Sigma). HA3 was purified using StrepTrap HP (GE Healthcare).

The recombinant proteins thus purified respectively were mixed together at a molar ratio of HA1:HA2:HA3=4:4:1. After this was incubated at 37° C. for three hours, it was purified with StrepTrap HP and thus HA complex was obtained.

TABLE 1

(Table 1)

| | | Mutation Site |
|---|---|---|
| Type B Wild-Type HA Complex | | — |
| Type B Mutant | 1 | HAI_ N286A |
| HA Complex | 2 | HA3 R528A |
| | 3 | HA1 N286A/HA3 R528A |
| | 4 | HA 3K607A |

Example 2

[Effect of Type B Mutant HA Complex on iPS Cells]

iPS cells were seeded on feeder cells (day 0), and the culture medium was exchanged with a maintenance medium every 24 hours. At three days after the start (day 3), an HA complex (a wild-type HA complex or a mutant HA complex) was added, and incubation was carried out for 24 hours. After this was washed with phosphate buffered saline (PBS) twice, the culture medium was exchanged with a maintenance medium (day 4). Thereafter, until nine days after the start (day 9), the culture medium was exchanged with a maintenance medium every 24 hours. After the culture, the expression of Oct3/4 of the cultured cells was checked by immunocytostaining. The cells, media, and culture conditions used herein are as follows.

<Cells> iPS Cells: Tic NP29 (those obtained by subculturing Tic that had been maintained with MEF)

Feeder Cells: SNL 76/7

<Medium> iPS Cells: Repro Stem (trade name, manufactured by ReproCELL Inc.), 5 ng/mL bFGF (Manufactured by ReproCELL Inc.)

Feeder Cells: DMEM (manufactured by SIGMA Corporation) (7% FBS (manufactured by GIBCO), 1% Penicillin-streptomycin solution (manufactured by NACALAI TESQUE))

<Vessel>

12-Well Plate (Culture Area: 3.8 $cm^2$/well, manufactured by Corning Inc.)

<HA Preparing and Adding Method>

The HA complexes each were serially diluted with PBS and were further diluted using a medium (Repro Stem) (final concentration: 100 nM). Further bFGF (final concentration: 5 ng/ml) was added thereto, which then was added to the wells.

<Culture Conditions>

5% $CO_2$ atmosphere at 37° C.

After the subculture of iPS cells, in exchanging the culture medium at three days after the start (day 3), the HA complex was added at respective concentrations, which was followed by culturing for 24 hours. Thereafter, in exchanging the culture medium at four days after the start (day 4), the medium was switched to a HA complex-free medium, and the culture was continued.

<Observation>

At day 3, day 4, day 5, and day 9, the cultured cells were observed with IN Cell Analyzer 2000 (trade name, manufactured by GE healthcare Bio-Sciences Corp.) and images thereof were acquired. The micrographs thus obtained are shown in FIGS. 1 to 4. In FIGS. 1 to 4, the part enclosed by the solid line in each upper image is shown in the image therebelow.

Comparative Example 1

Figure 5:
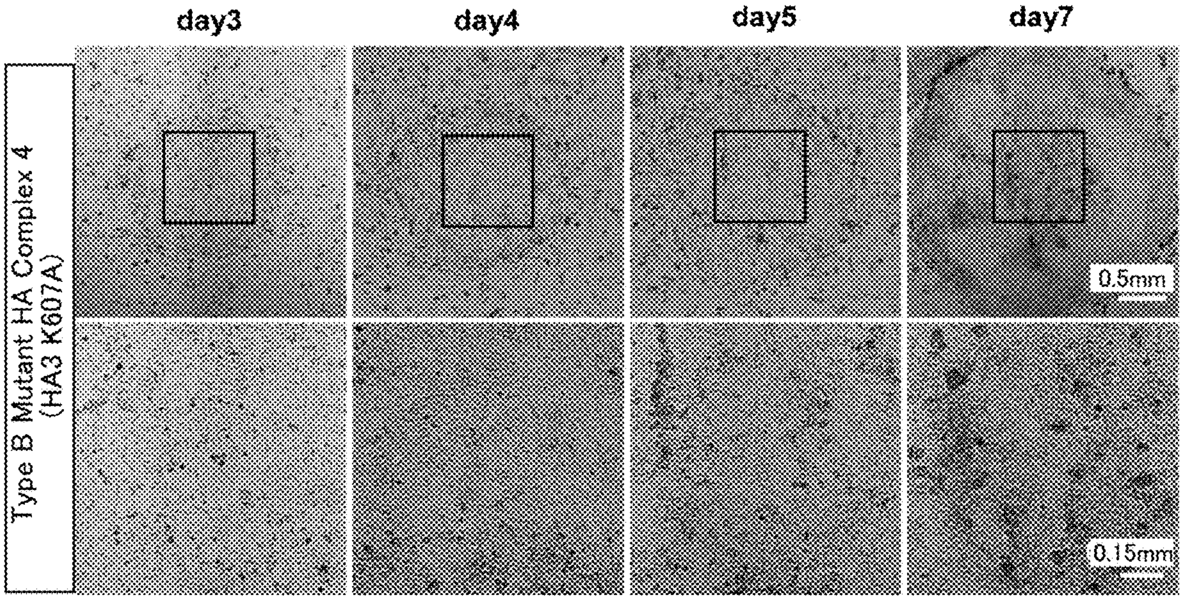
FIG. 5 shows exemplary micrographs of iPS cell colonies in the case where a type B mutant HA complex 4 (HA3 K607A) was added at day 3 (Comparative Example 1).

Using the mutant HA complex 4 (HA3 K607A), the same experiment as in Example 2 was carried out. FIG. 5 shows the result. In FIG. 5, the part enclosed by the solid line in each upper image is shown in the image therebelow.

Figure 2:
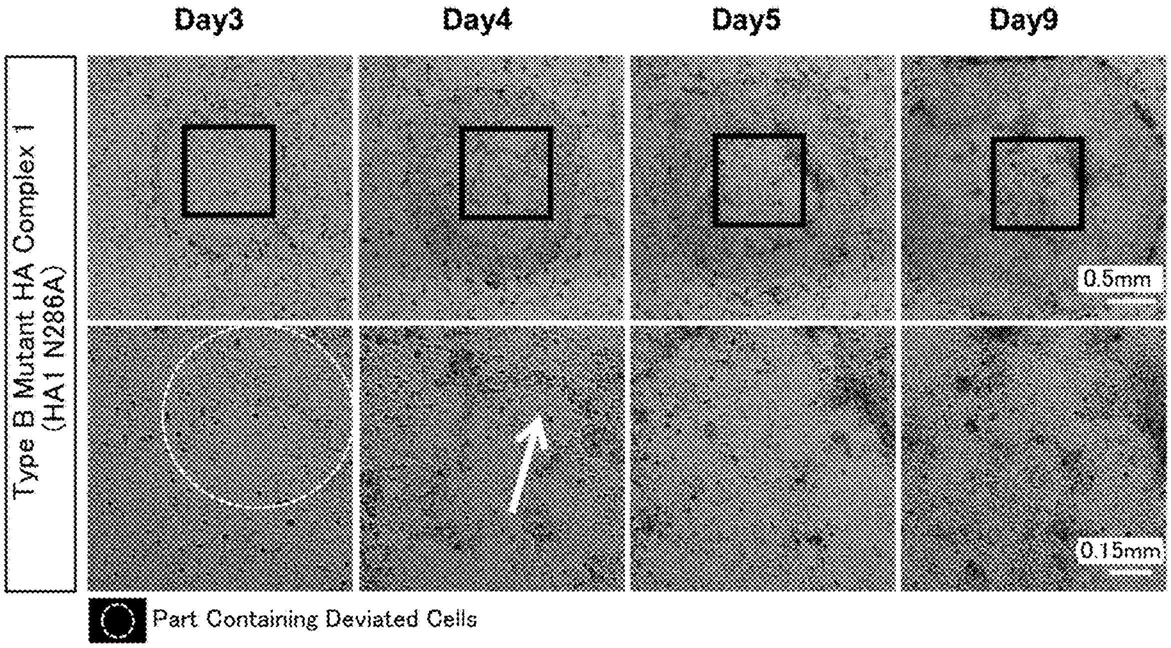
FIG. 2 shows exemplary micrographs of iPS cell colonies in the case where a type B mutant HA complex 1 (HA1 N286A) was added at day 3 (Example 2).
Figure 3:
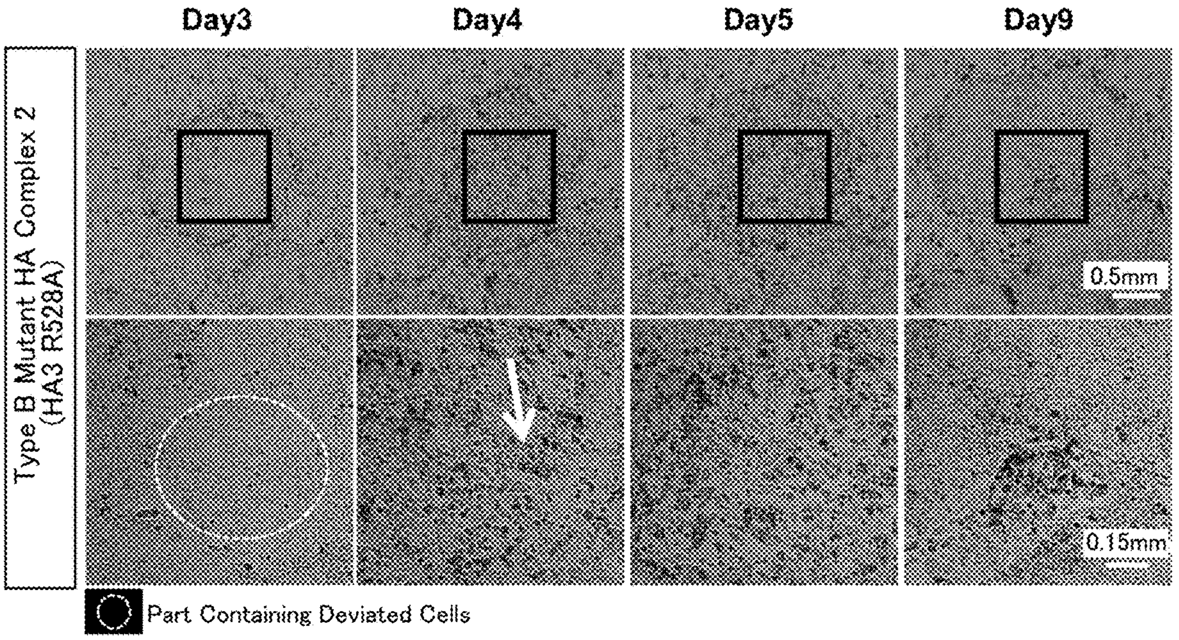
FIG. 3 shows exemplary micrographs of iPS cell colonies in the case where a type B mutant HA complex 2 (HA3 R528A) was added at day 3 (Example 2).
Figure 4:
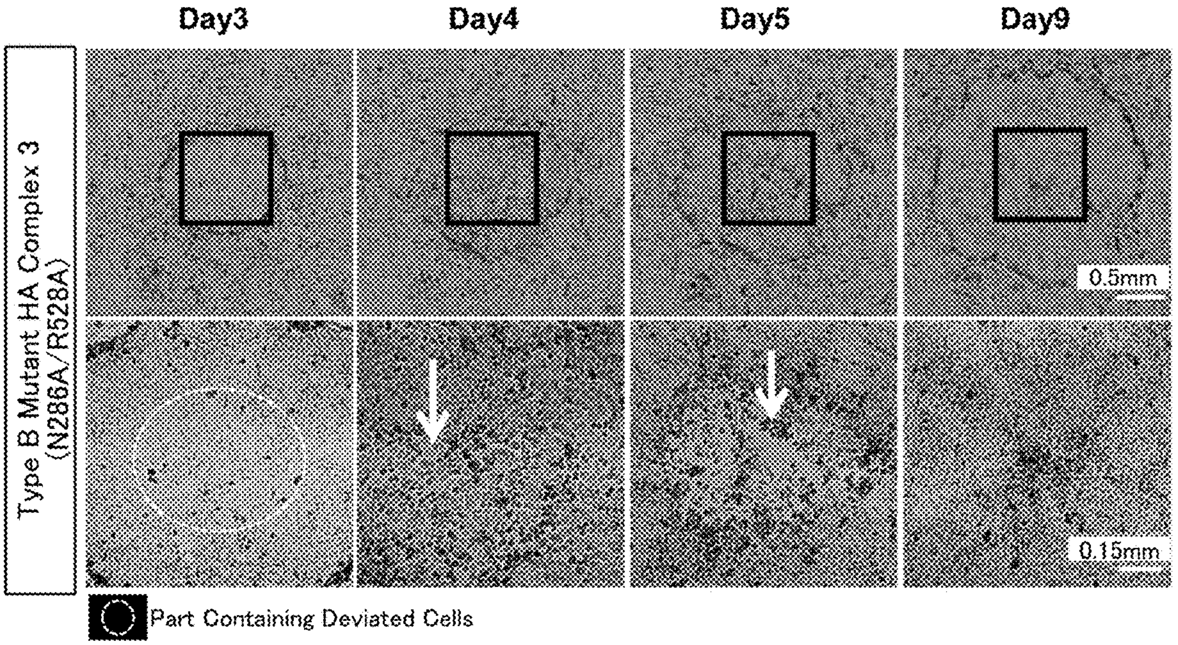
FIG. 4 shows exemplary micrographs of iPS cell colonies in the case where a type B mutant HA complex 3 (HA1 N286A/HA3 R528A) was added at day 3 (Example 2).

FIG. 1 shows micrographs of the wild-type HA complex, FIG. 2 shows micrographs of the mutant HA complex 1, FIG. 3 shows micrographs of the mutant HA complex 2, and FIG. 4 shows micrographs of the mutant HA complex 3.

The asbaragine at position 286 in the subcomponent HA1 and the arginine at position 528 in the HA3 are known to be carbohydrate recognition sites. As shown in FIGS. 2 to 4, with respect to each of the mutant HA complexes 1 to 3, in which glycosylation activity had been deleted, the cell-cell adhesion of deviated cells was weakened at 24 hours after the addition of the mutant HA complexes (day 3). Thus, the inhibition of the cell-cell adhesion of deviated cells was confirmed. Particularly, in the case of the mutant HA complex 2 (HA3 R528A), not only the inhibition of the cell-cell adhesion of deviated cells at the colony center but also cell detachment was observed. Furthermore, in the case of the mutant HA complex 3 (HA1 N286A/HA3 R528A), as shown in FIG. 4, the cell-cell adhesion was weakened at 24 hours after the addition of the mutant HA complex (day 3), and a higher effect in cell detachment was observed (the part indicated with the arrow in FIG. 4) at 48 hours after the addition (day 4) as compared to other mutant HA s and the wild-type HA. Moreover, it was found that a colony where an undifferentiated state was maintained was formed at nine days after the start of the culture (day 9). On the other hand, in the case of the mutant HA complex 4 (HA3 K607A) of Comparative Example 1, which was a cadherin-binding activity-deficient mutant, inhibition of cell-cell adhesion or cell detachment was not observed (FIG. 5). Thus, it was suggested that the mutant HA complexes 1 to 3, in which the glycosylation activity has been deleted, are able to inhibit local cell-cell adhesion and particularly the mutant HA complexes 2 and 3 are able to efficiently detach deviated cells.

The colonies were stained with DAPI and an undifferentiation marker (Oct3/4, TRA-1-60, and SSEA-4) or an endoderm, mesoderm, or ectoderm early differentiation marker (α-SAM, Serum albumin, or Nestin). As a result, it was found that the deviated cells that had emerged at the colony center were negative for both the undifferentiation marker and the above-mentioned early differentiation marker and the cells therearound were positive for the undifferentiation marker.

Example 3

[Effect of Type B HA Complex on iPS Cells (Part 2)]

Wild-type HA complexes 1 to 5 were produced in the same procedure as in Example 1 except that tags were bound to different sites as indicated in Table 2 below.

Figure 6:
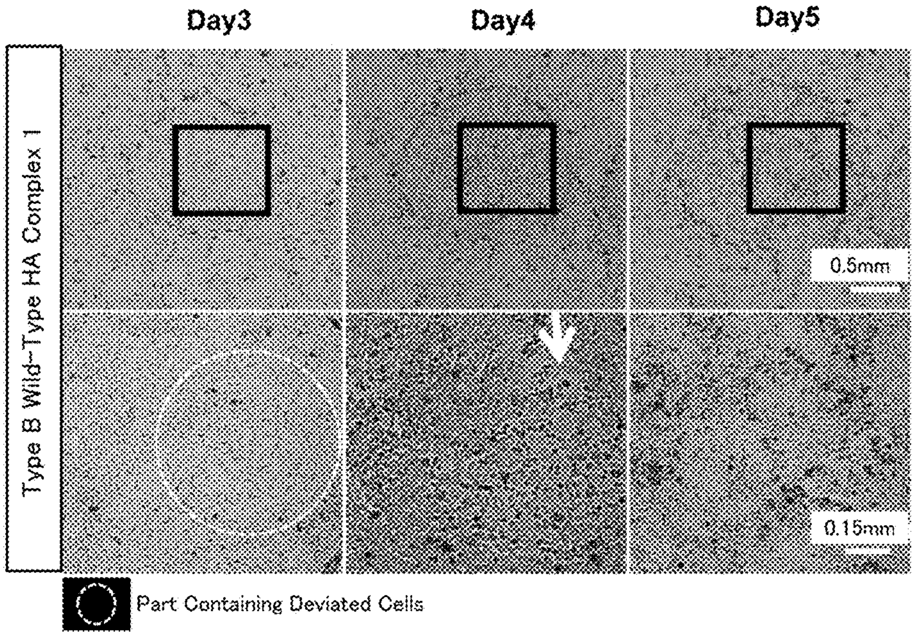
FIG. 6 shows exemplary micrographs of iPS cell colonies in the case where a type B wild-type HA complex 1 was added at day 3 (Example 3).
Figure 7:
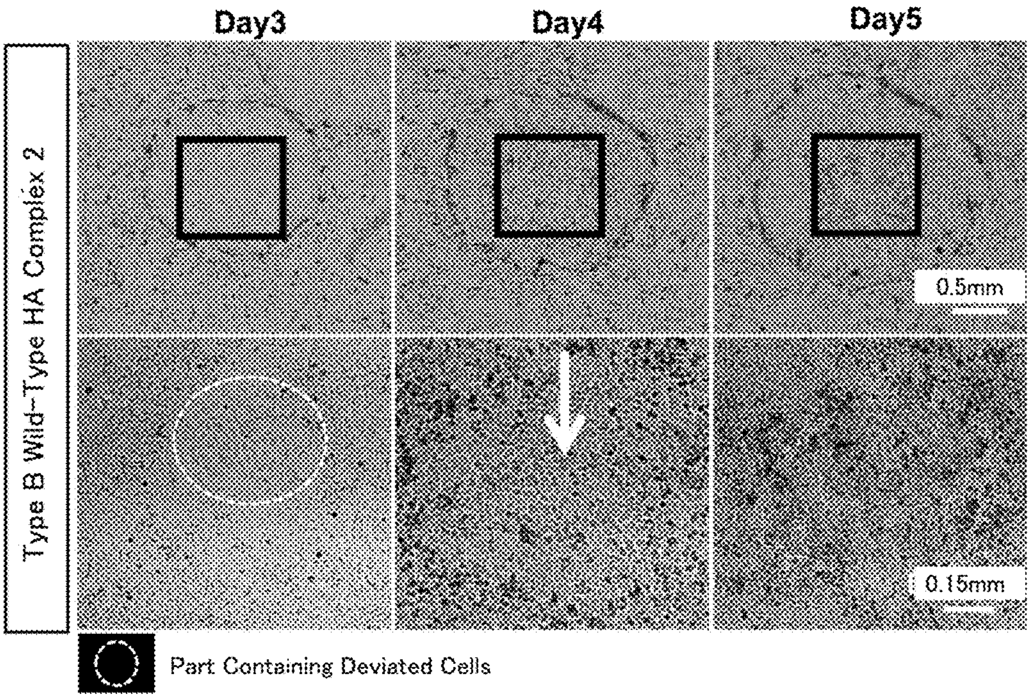
FIG. 7 shows exemplary micrographs of iPS cell colonies in the case where a type B wild-type HA complex 2 was added at day 3 (Example 3).
Figure 8:
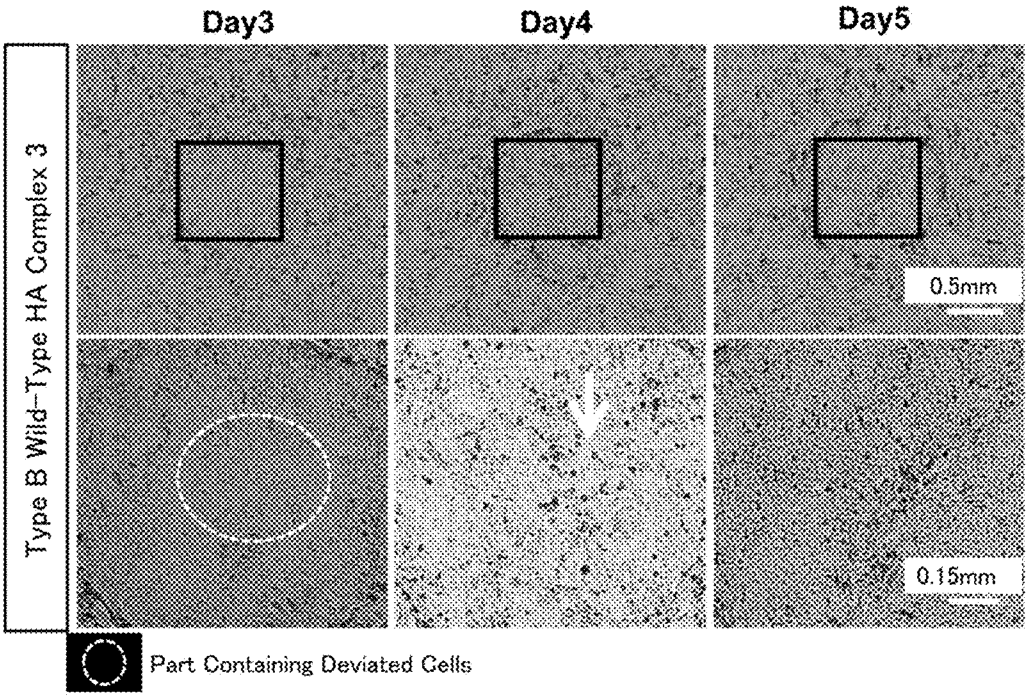
FIG. 8 shows exemplary micrographs of iPS cell colonies in the case where a type B wild-type HA complex 3 was added at day 3 (Example 3).
Figure 9:
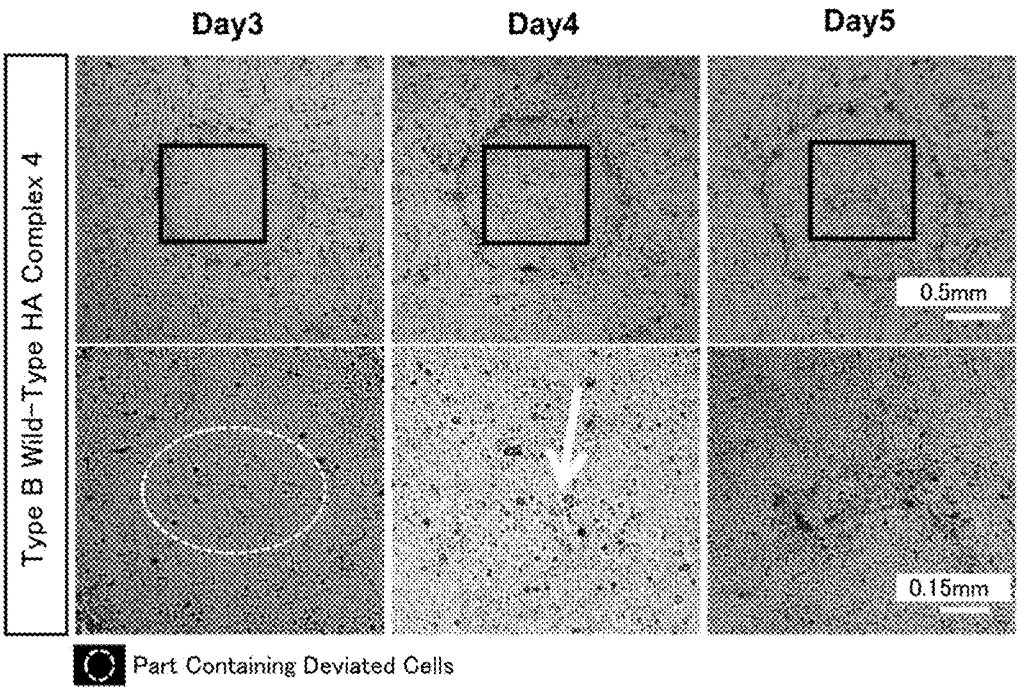
FIG. 9 shows exemplary micrographs of iPS cell colonies in the case where a type B wild-type HA complex 4 was added at day 3 (Example 3).
Figure 10:
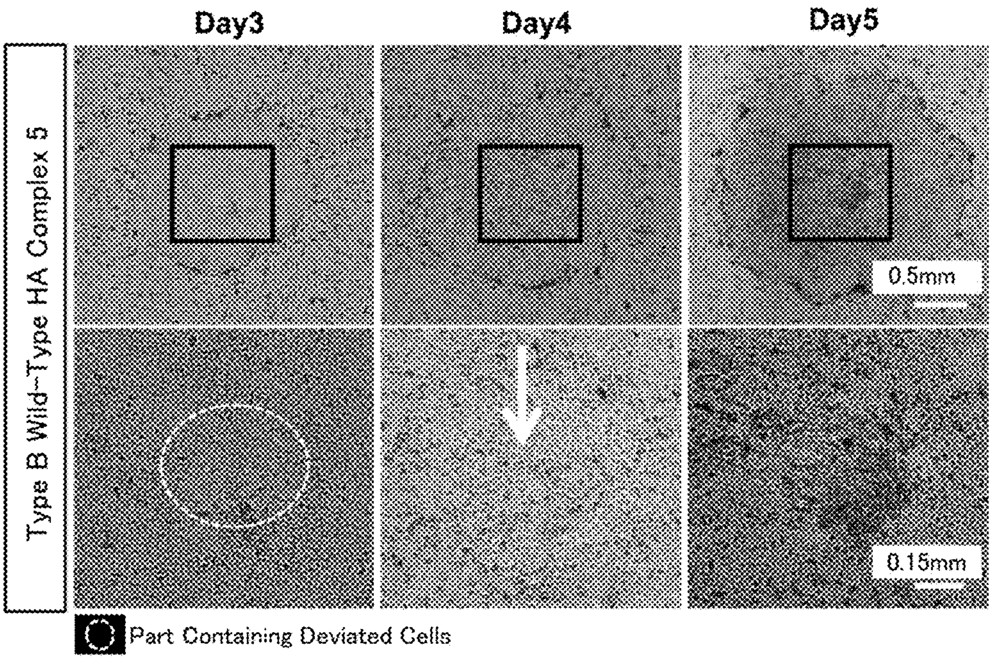
FIG. 10 shows exemplary micrographs of iPS cell colonies in the case where a type B wild-type HA complex 5 was added at day 3 (Example 3).

The wild-type HA complexes 1 to 5 thus prepared were used to check the effects thereof on iPS cells in the same manner as in Example 2. FIGS. 6 to 10 show the results. FIG. 6 shows micrographs of the wild-type HA complex 1, FIG. 7 shows micrographs of the wild-type HA complex 2, FIG. 8 shows micrographs of the wild-type HA complex 3, FIG. 9 shows micrographs of the wild-type HA complex 4, and FIG. 10 shows micrographs of the wild-type HA complex 5.

TABLE 2

(Table 2)

| | | Tag (Binding Site, Type) | | |
|---|---|---|---|---|
| | | HA1 | HA2 | HA3 |
| Type B Wild-Type HA Complex | 1 | C-Terminal FLAG | N-Terminal FLAG | N-Terminal Strep |
| | 2 | N-Terminal FLAG | N-Terminal FLAG | N-Terminal Strep |
| | 3 | N-Terminal FLAG | N-Terminal His | N-Terminal Strep |
| | 4 | C-Terminal FLAG | N-Terminal His | N-Terminal Strep |
| | 5 | N-Terminal His/ C-Terminal FLAG | N-Terminal His | N-Terminal Strep |

As shown with the arrows in FIGS. 6 to 10, in all the wild-type HA complexes, weakening of the cell-cell adhesion (inhibition of the cell-cell adhesion) of deviated cells was observed at 24 hours after the addition of the wild-type HA complexes (day 3). Especially, in the wild-type HA complexes 1, 3, and 4, cell detachment was observed at 24 hours after the addition (day 3), and particularly, in the wild-type HA complex 1, it was observed at five days after the start of the culture (day 5) that deviated cells had been removed and a colony where an undifferentiated state had been maintained had been formed. Therefore, it was suggested that the wild-type HA complex 1 allows deviated cells to be efficiently detached.

Example 4

[Effect of Type B Mutant HA Complex on iPS Cell Cluster (Part 1)]

Using a 96-well V-bottom plate, iPS cell clusters were prepared, and half of the culture medium was exchanged daily. The HA complex was added to the iPS cell clusters at three days after the start of the culture (day 3). At four days after the start of the culture (day 4), iPS cell clusters were transferred to a 96-well plate flat bottom plate and then were lightly pipetted, and thereby it was checked whether the cell clusters were divided. The cells, medium, HA complexes, culture conditions, and the like that were used herein are as follows.

<Cells>

Human iPS Cells (Tic NP41 (iPS cells that had been maintained with iMatrix-511 (nippi)))

<Medium> mTeSR1 (STEMCELL Technologies)

<Vessel>

96-Well V-Bottom Plate (Sumitomo Bakelite)

<HA>

Wild-Type HA Complex

Mutant HA Complex 1 (HA1 N286A)

Mutant HA Complex 2 (HA3 R528A)

Mutant HA Complex 3 (HA1 N286A/HA3 R528A)

Mutant HA Complex 4 (HA3 K607A)

<HA Preparing and Adding Method>

The HA complexes each were serially diluted with PBS and were further diluted using a medium (mTeSR1). This (final concentration: 100 nM) was added to the wells.

<Culture Conditions>

5% $CO_2$ atmosphere at 37° C.

<Observation>

Using In Cell Aanalyzer (trade name, manufactured by GE healthcare Bio-Sciences Corp.), the cell clusters were observed in the entire visual field and images thereof were acquired. Imaging was carried out at 4× magnification before and after the addition of the mutant HA complexes (day 3 and day 4). The micrographs thus obtained were shown in FIGS. 11 and 12.

Divided cell clusters were cultured on a laminin-coated culture surface (feeder cells: SNL), and all the culture medium was exchanged daily. At five days after the start of the culture, while cell morphology was observed, the expression of Oct3/4 of the cultured cells was checked by immunocytostaining using a mouse monoclonal Oct3/4 antibody (Santa Cruz Biotechnology, sc-5279), and further, DAPI staining was performed.

As a control, the same procedure as described above was carried out, except that the HA complexes were not added. The above results are indicated in Table 3 below.

TABLE 3

(Table 3)

| | | Mutation Site | Cluster Breakup Effect |
|---|---|---|---|
| Type B Wild-Type HA Complex | | — | ○ |
| Type B Mutant HA Complex | 1 | HA1 N286A | ◎ |
| | 2 | HA3 R528A | ◎ |
| | 3 | HA1 N286A/ HA3 R528A | ◎ |
| | 4 | HA3 K607A | Δ |
| Control | | — | x |

[Evaluation Criteria]

◎: Cell clusters were able to be divided into smaller blobs.

○: Cell clusters were able to be divided.

Δ: Division of cell clusters was hardly observed.

x: Cell clusters were not divided.

Figure 11:
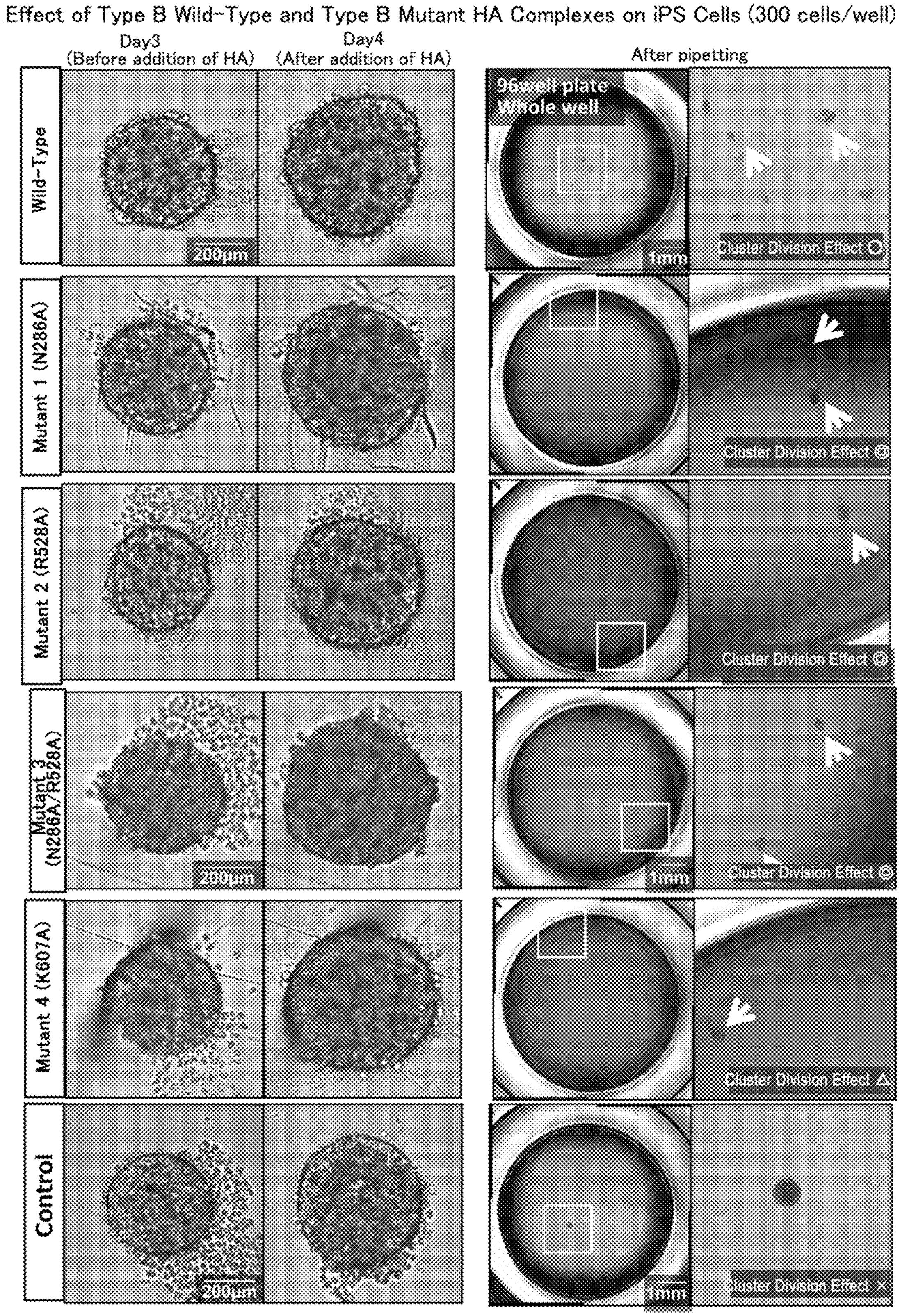
FIG. 11 shows exemplary micrographs of cell clusters of iPS cells in the case where a type B wild-type HA complex and type-B mutant HA complexes were added in suspension culture (300 cells/well, Example 4).
Figure 12:
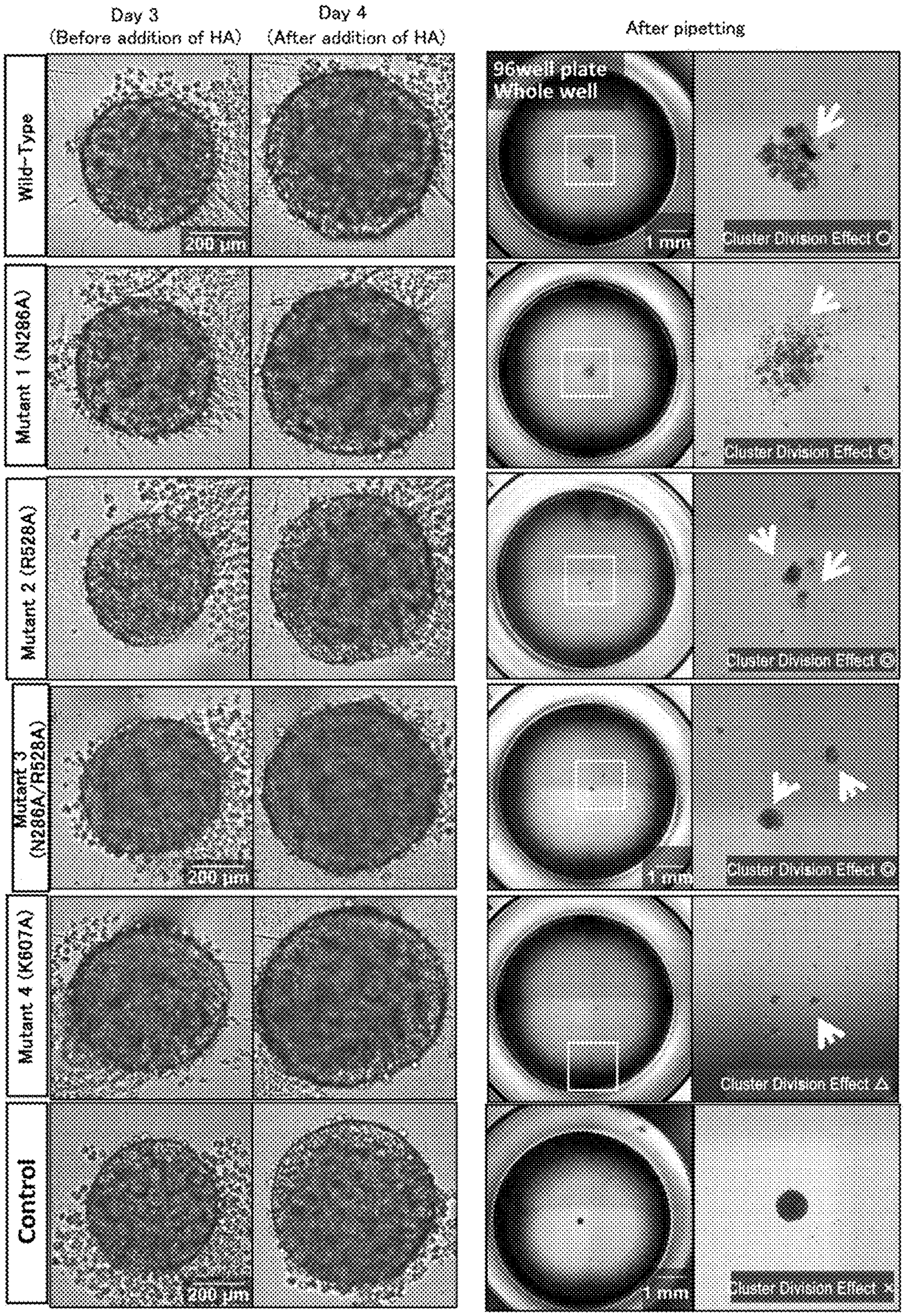
FIG. 12 shows exemplary micrographs of cell clusters of iPS cells in the case where a type B wild-type HA complex and type-B mutant HA complexes were added in suspension culture (500 cells/well, Example 4).

As shown in FIGS. 11 and 12, addition of the wild-type HA complex and the mutant HA complexes 1 to 3 allowed the human iPS cell clusters to be divided into smaller cell clusters. Particularly, addition of the mutant HA complexes 1 to 3 allowed the human iPS cell clusters to be divided further smaller blobs. On the other hand, in the case of addition of the mutant HA complex 4 (HA3 K607A) of Comparative Example 1, which was a cadherin-binding activity-deficient mutant, hardly any division of the cell clusters was observed, and in the case of the control (with no HA complex added), the cell clusters were not divided.

Example 5

[Effect of Type B HA Complex on iPS Cell Cluster (Part 2)]

Figure 13:
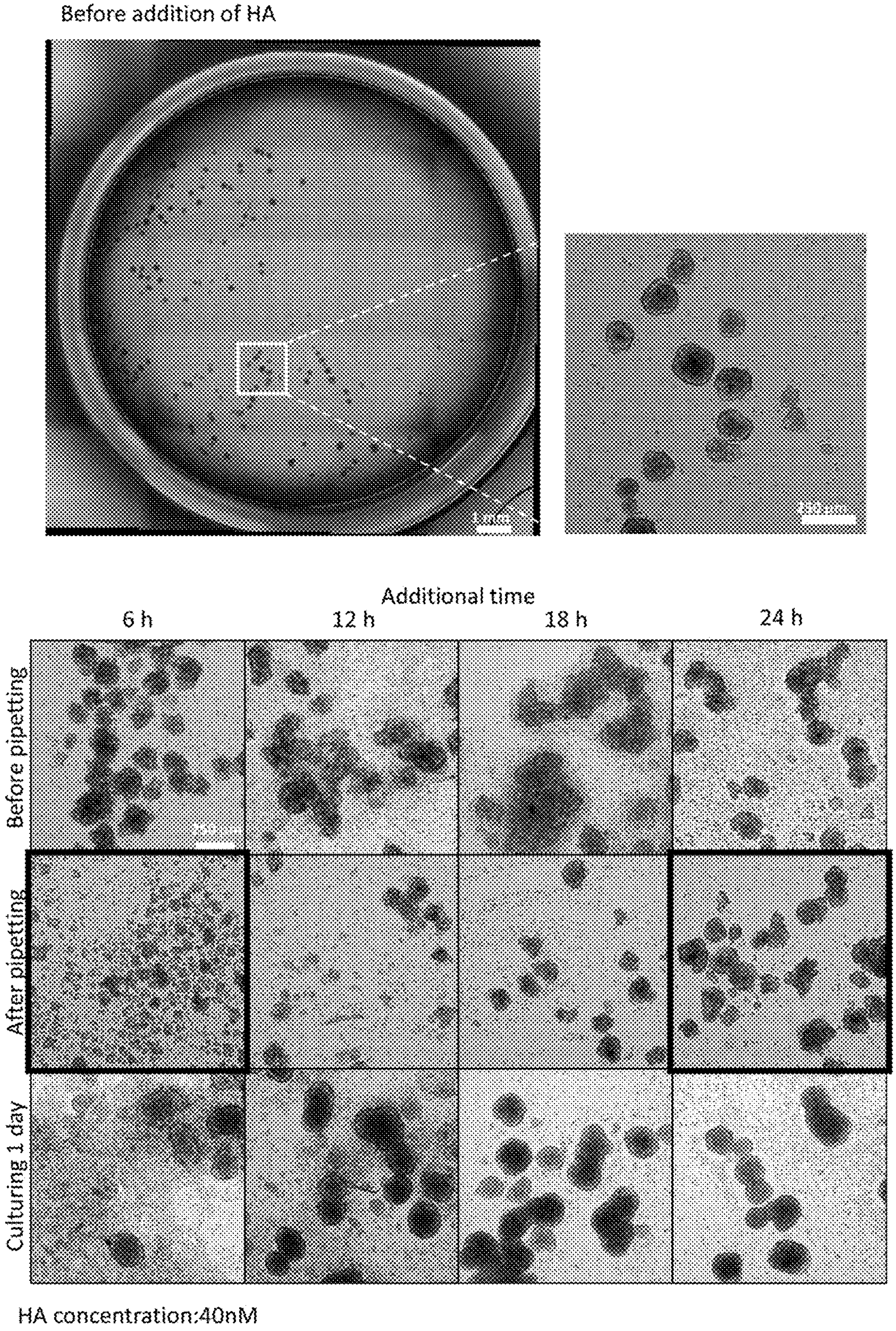
FIG. 13 shows exemplary micrographs of cell clusters of iPS cells at the various points of time (6, 12, 18, and 24 hours) when a type B wild-type HA complex was added in suspension culture (Example 5).

For preculture, iPS cells were cultured with a 30 nil reactor for five days. The cells at five days after the start of the culture were transferred to a 24-well plate and then an HA complex was added thereto. At 6, 12, 18, or 24 hours after the addition of the HA complex, the culture medium was exchanged to remove HA, and then cell clusters were divided by pipetting. Thereafter, culture was performed for 24 hours, and then the morphology of the cell clusters was observed. The cells, medium, HA, culture conditions, and the like that were used herein are as follows. The micrographs obtained herein are shown in FIG. 13.

<Cells>

Human iPS Cells (Tic, National Center for Global Health and Medicine, Np. 52)

<Medium> mTeSR1 (Cata #0580/05896, STEMCELL TECHNOLOGIES)

<Culture Environment>

5% $CO_2$ atmosphere at 37° C.

<Culture Vessel>

24-Well Plate (Corning, Cat. No. 3526)

<Seeding Density>

$1.0\times10^5$ cells/ml

<HA>

Wild-Type HA Complex 5 (His-BHA1-FLAG:His-BHA2:Strep-BHA3) Concentration of added Complex: 40 nM <Observing Device>

IN Cell Analyzer (GE Healthcare)

Addition of the HA complex divided cell clusters into smaller clusters, which were then cultured, and thereby aggregates were formed again as shown in FIG. 13. Furthermore, with respect to the period of time when the HA complex was being added (the period of time from the addition of HA until the exchange of the culture medium), the following tendency was observed: when the period was six hours, the degree of division was highest, while when the period was 12 hours or longer, division became difficult. This suggested the possibility that the HA complex in the medium is digested or inactivated by, for example, endocytosis of the cells. Therefore, it was suggested that even when the HA removal procedure is not performed after cell clusters are divided with the HA complex, iPS cells can be reaggregated to form cell clusters. On the other hand, with respect to the HA complex added into the medium, an adsorption column that uses a tag attached to the HA complex as the target is provided and the medium is circulated, and thereby the HA complex can be forcibly recovered from the medium. Thus, since the HA complex can spontaneously or forcibly be removed/recovered, effects of removing deviated cells and dividing cell clusters can be timely exhibited temporarily or continuously. This suggested that automatic operation using a bioreactor is possible.

Example 6

[Effect of Type B Mutant HA Complex on iPS Cell Cluster (Part 3)]

Figure 14:
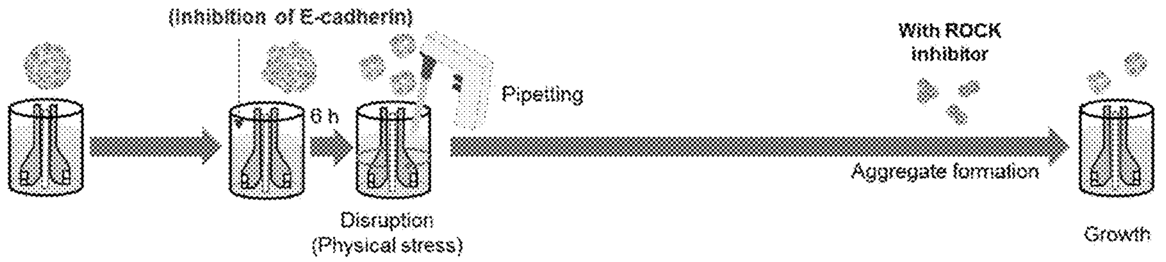
FIG. 14 explains a flow of the experiment carried out in Example 6.
Figure 15:
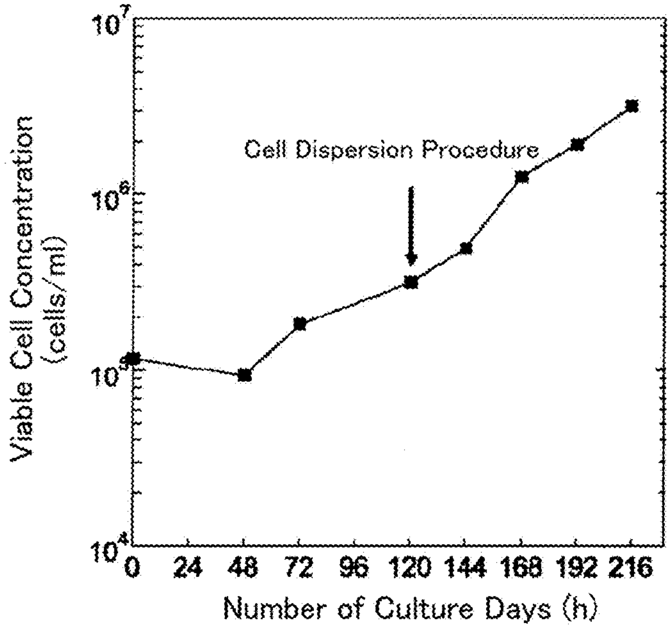
FIG. 15 illustrates an exemplary graph showing the relationship between the number of culture days and viable cell concentration in Example 6.

According to the procedure shown in FIG. 14, iPS cells were cultured. First, iPS cells were subjected to suspension culture using a bioreactor for 120 hours and thereby cell clusters of the iPS cells were formed. Subsequently, a type B mutant HA complex was added thereto, which then was subjected to HA treatment for six hours. Thereafter, the cell clusters were divided by pipetting. Then, 10 μM of ROCK inhibitor was added thereto, which then was further subjected to suspension culture. Furthermore, the viable cell concentration was measured every 24 hours. An example of the results is shown in FIG. 15.

<Cells>

Human iPS Cells (Tic, National Center for Global Health and Medicine, Np. 52)

<Medium> mTeSR1 (Cata #0580/05896, STEMCELL TECHNOLOGIES)

<Culture Environment>

5% $CO_2$ atmosphere at 37° C.

<Culture Vessel>

24-Well Plate (Corning, Cat. No. 3526)

<Seeding Density>

$1.0\times10^5$ cells/ml

<HA>

Type B Mutant HA Complex (Tag (Binding Site, Type) HA1: C-terminal FLAG, HA2: N-terminal FLAG, HA3: N-terminal Strep)

Concentration of added Complex: 10 nM

<Observing Device>

IN Cell Analyzer (GE Healthcare)

It was observed that cell clusters divided into small blobs by pipetting carried out after HA treatment were reaggregated by subsequent culture to form cell clusters. Therefore, it was suggested that the HA complex is digested or inactivated by, for example, endocytosis of cells. Furthermore, as shown in FIG. 15, it was confirmed that the viable cell concentration increased with an increase in the number of culture days. Thus, the use of the cell dividing operation performed by HA treatment made it possible to achieve a process for culturing iPS cells at a high density.

Example 7

[Effect of Type B Mutant HA Complex on iPS Cell Cluster (Part 4)]

Figure 16:
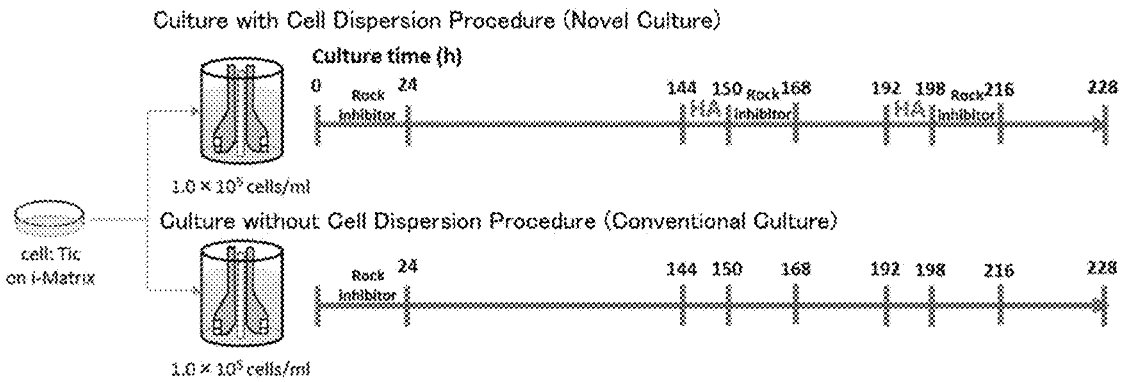
FIG. 16 explains a flow of the experiment carried out in Example 7.
Figure 17:
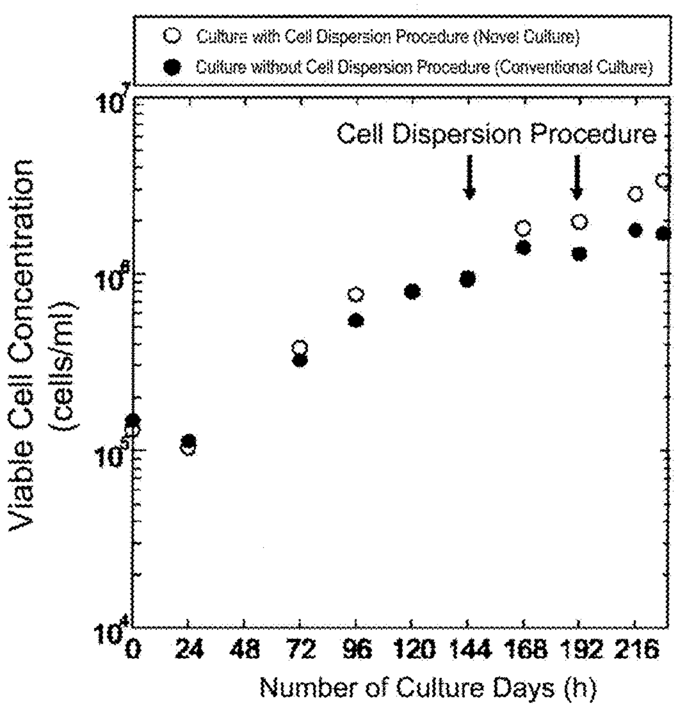
FIG. 17 illustrates an exemplary graph showing the relationship between the number of culture days and viable cell concentration in Example 7.

According to the procedure shown in FIG. 16, iPS cells were cultured. First, iPS cells were placed in a bioreactor and then 10 μM of ROCK inhibitor was added thereto, which was subjected to ROCK inhibitor treatment for 24 hours. Thereafter, it was subjected to suspension culture for 120 hours and thereby cell clusters of the iPS cells were formed. Subsequently, a type B mutant HA complex was added thereto, which then was subjected to HA treatment for six hours. Thereafter, the cell clusters were divided by pipetting. Then, 10 μM of ROCK inhibitor was added thereto, which then was subjected to ROCK inhibitor treatment for 18 hours. This was further subjected to suspension culture for 12 hours. The culture medium was exchanged and the viable cell concentration was measured every 24 hours. An example of the results is shown in FIG. 17.

<Cells>

Human iPS Cells (Tic, National Center for Global Health and Medicine, Np. 52)

<Medium> mTeSR1 (Cata #0580/05896, STEMCELL TECHNOLOGIES)

<Culture Environment>

5% $CO_2$ atmosphere at 37° C.

<Culture Vessel>

24-Well Plate (Corning, Cat. No. 3526)

<Seeding Density>

$1.0\times10^5$ cells/ml

<HA>

Type B Mutant HA Complex (Tag (Binding Site, Type) HA1: C-terminal FLAG, HA2: N-terminal FLAG, HA3: N-terminal Strep)

Concentration of added Complex: 10 nM

<Observing Device>

IN Cell Analyzer (GE Healthcare)

As a control, as shown in FIG. 16, iPS cells were cultured by a normal subculture method. That is, iPS cells were cultured in the same manner as in Example 7 except that HA treatment and ROCK inhibitor treatment at 150 hours and 198 hours after the start of the culture were not performed. An example of the results is shown in FIG. 17.

In Example 7, division of cell clusters by pipetting after HA treatment and reaggregation of cell clusters by the subsequent culture were observed. As shown in FIG. 17, in both Example 6 and the control, the viable cell concentration increased from 24 hours after the start of the culture and rapid proliferation was observed. However, proliferation rate decreased gradually around 144 hours after the start of the culture. In the control that was not subjected to HA treatment, proliferation (an increase in viable cell concentration) slowed down from 144 hours, and proliferation was hardly observed, with the viable cell concentration being around $1.5\times10^6$ cells/ml from 168 hours. On the other hand, in Example 6 in which HA treatment was performed at 144 hours after the start of the culture, the proliferation rate that had decreased by one degree was restored, and cell proliferation was observed even at 144 hours or later. Furthermore, the second HA treatment was performed at 192 hours after the start of the culture. As a result, restoration of the gradual proliferation rate was observed, and the final viable cell concentration after 216 hours of culture was $3.36\times10^6$ cells/ml in the case of Example 6 ($1.68\times10^6$ cells/ml in the case of the control). Thus, it was found that as compared to the normal subculture method, in the culture method that utilizes a cell division operation performed by HA treatment, cell proliferative capacity was maintained and high-density culture of iPS cells was possible.

Example 8

[Effect of Type a Mutant HA Complex on iPS Cells]

The type A wild-type HA complex and the type A mutant HA complexes indicated in Table 4 below were produced. These HA complexes were produced based on T. Matsumura et al., Nature Communications 2015 Feb. 17; 6:6255. doi: 10.1038/ncomms7255. With respect to the protein of each subcomponent used in preparing plasmids, HA1 was a recombinant protein with a FLAG-tag binding to the C-terminal thereof, HA2 was a recombinant protein with a FLAG-tag binding to the N-terminal thereof, and HA3 was a recombinant protein with a Strep-tag binding to the N-terminal thereof.

TABLE 4

(Table 4)

| | | Mutation Site |
|---|---|---|
| Type A Wild-Type HA Complex | | — |
| Type A Mutant | 2 | HA3 R528A |
| HA Complex | 3 | HA1 N285A/HA3 R528A |
| | 4 | HA3 K607A |
| Control | | — |

iPS cells were seeded on feeder cells (day 0), and the culture medium was exchanged with a maintenance medium every 24 hours. At three days after the start (day 3), the HA complex (the type A wild-type HA complex or type A mutant HA complex) was added, which then was incubated for 24 hours. After this was washed with PBS twice, the culture medium was exchanged with a maintenance medium (day 4). Thereafter, until seven days later (day 7), the culture medium was exchanged with a maintenance medium every 24 hours. The cells, media, and culture conditions used herein are as follows.

<Cells> iPS Cells: Tic (Tic that had been maintained with MEF was subcultured, which then was seeded on SNL cells; NP13)

Feeder Cells: SNL

<Medium> iPS cells: Repro Stem (trade name, manufactured by ReproCELL Inc.), 5 ng/mL bFGF (Manufactured by ReproCELL Inc.)

Feeder Cells: DMEM (Manufactured by SIGMA Corporation) (7% FBS (manufactured by Gibco), 1% Penicillin-streptomycin solution (manufactured by NACALAI TESQUE))

<Vessel>

12-Well Plate (Culture Area: 3.8 $cm^2$/well, manufactured by Corning Inc.)

<HA Preparing and Adding Method> bFGF (final concentration: 5 ng/ml) was added to a medium (Repro Stem) and thereby a diluted medium was prepared. The type A mutant HA complexes 2 to 4 indicated in Table 4 above were diluted using the diluted medium (final concentration: 100 nM), which then were added to the wells.

<Culture Conditions>

5% $CO_2$ atmosphere at 37° C.

After the subculture of iPS cells, in exchanging the culture medium at three days after the start (day 3), the HA complex was added, which was followed by culturing for 24 hours. Thereafter, in exchanging the culture medium at four days after the start (day 4), the medium was switched to a HA complex-free medium, and the culture was continued.

<Observation>

Figure 18:
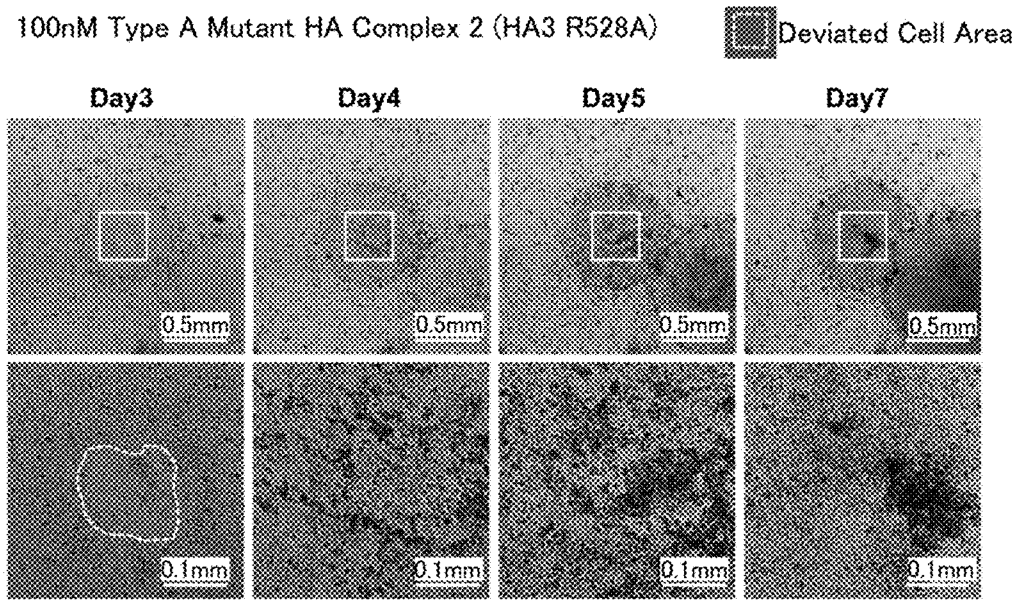
FIG. 18 shows exemplary micrographs of iPS cell colonies in the case where a type A mutant HA complex 2 (HA3 R528A) was added at day 3 (Example 7).
Figure 19:
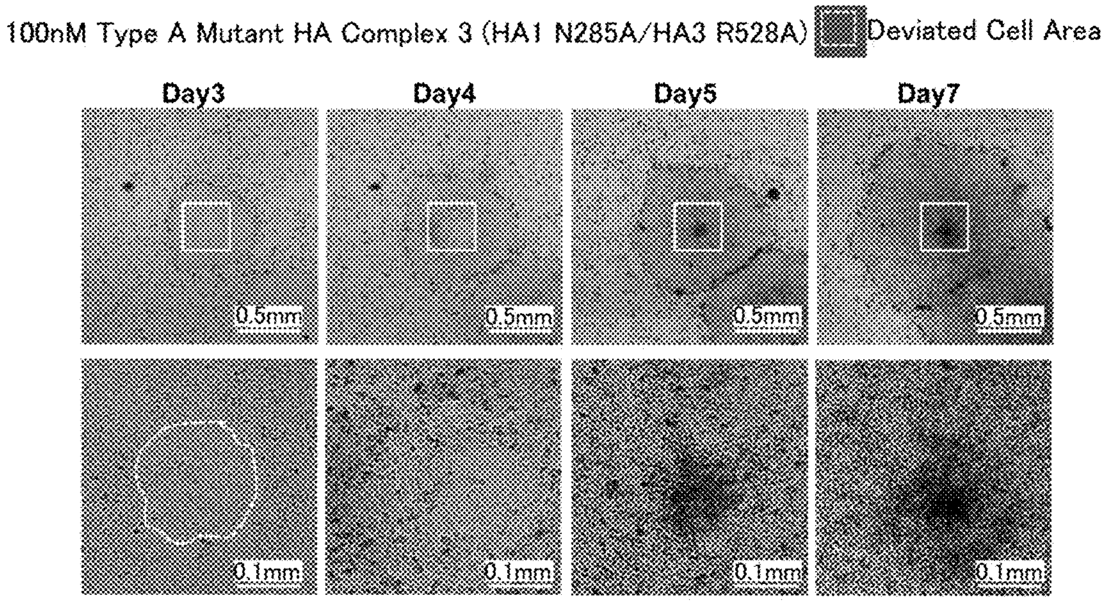
FIG. 19 shows exemplary micrographs of iPS cell colonies in the case where a type A mutant HA complex 3 (HA1 N285A/HA3 R528A) was added at day 3 (Example 7).
Figure 20:
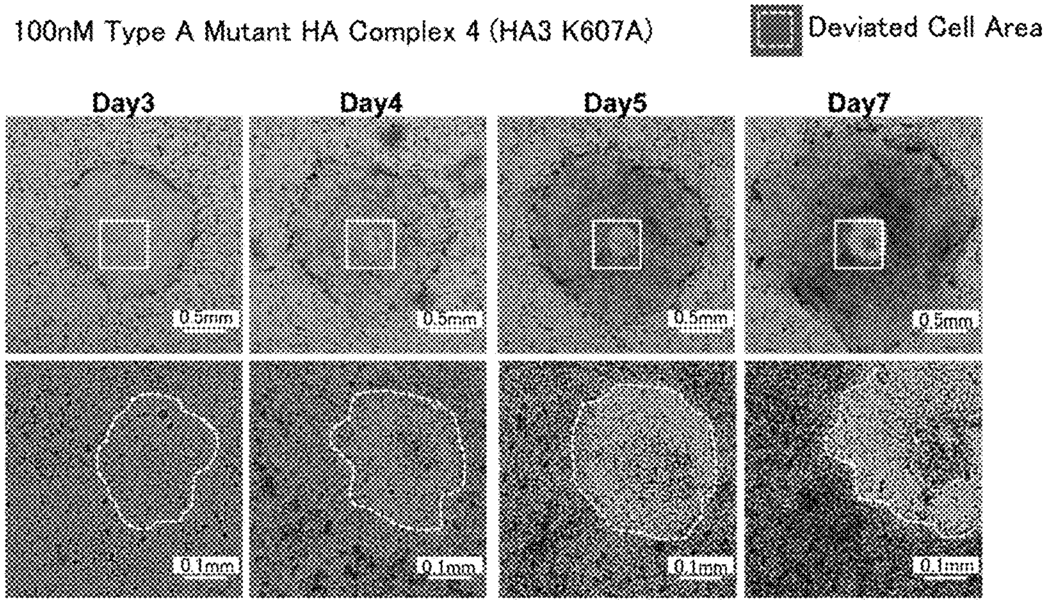
FIG. 20 shows exemplary micrographs of iPS cell colonies in the case where a type A mutant HA complex 4 (HA3 K607A) was added at day 3 (Comparative Example 3).

At day 3, day 4, day 5, and day 7, the cultured cells were observed with IN Cell Analyzer 2000 (trade name, manufactured by GE healthcare Bio-Sciences Corp.) and images were acquired. Imaging was carried out at 4× magnification. The micrographs thus obtained are shown in FIGS. 18 and 19. In FIGS. 18 to 20, the part enclosed by the solid line in each upper image is shown in the image therebelow.

FIG. 18 shows micrographs of the type A mutant HA complex 2 (HA3 R528A) and FIG. 19 shows micrographs of the type A mutant HA complex 3 (HA1 N285A/HA3 R528A).

Figure 21:
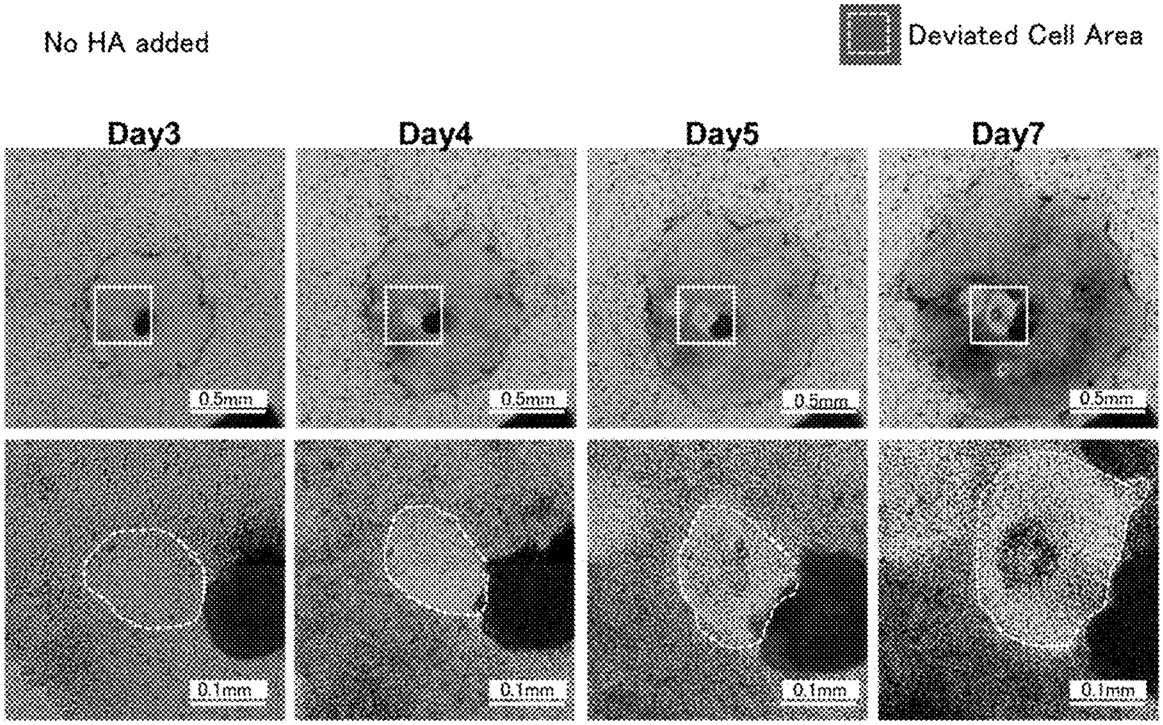
FIG. 21 shows exemplary micrographs of iPS cell colonies of a control (with no HA added).

As Comparative Example 3, iPS cells were cultured in the same manner as in the above-described example except for using a type A mutant HA complex 4 (HA3 K607A), which was a cadherin-binding activity-deficient mutant. As a control, iPS cells were cultured in the same manner as in the example except for adding no HA complex. The micrographs obtained herein are shown in FIGS. 20 and 21, respectively.

As shown in FIGS. 18 and 19, in both the type A mutant HA complexes 2 and 3 in which glycosylation activity had been deleted, at 24 hours after the addition of the type A mutant HA complex (day 3), cell-cell adhesion of deviated cells located at the colony center was weakened and thus inhibition of the cell-cell adhesion of the deviated cells was confirmed while cell detachment was observed. Particularly, in the case of the type A mutant HA complex 3 (HA1 N285A/HA3 R528A), as compared to the type A wild-type HA complex and the type A mutant HA complex 2, a higher cell detachment effect was observed. On the other hand, with respect to the control with no HA complex added thereto and the mutant HA complex 4 (HA3 K607A) of Comparative Example 3, which was a cadherin-binding activity-deficient mutant, neither inhibition of cell-cell adhesion nor cell detachment was observed (FIGS. 20 and 21). Thus, it was suggested that the type A mutant HA complexes 2 and 3, in which glycosylation activity has been deleted, are able to inhibit local cell-cell adhesion and are able to detach deviated cells efficiently.

Example 9

[Effect of Type a Mutant HA Complex on iPS Cell Cluster]

In a nonadherent medium vessel 60 mm dish (Thermo: Nunclon Sphere), iPS cells were seeded ($4.2\times10^6$ cells/60 mm dish) and cultured. Thus, iPS cell clusters were prepared. The culture medium was exchanged daily until four days after the start of the culture (day 4). At four days after the start of the culture (day 4), the iPS cell clusters were transferred to a 24-well plate and the photograph thereof was taken before addition of HA. Thereafter, each HA complex was added (final concentration: 40 nM). At 6, 12, 18, or 24 hours after the addition of HA, pipetting was performed. The cell clusters were observed before and after the pipetting while it was checked whether the cell clusters were divided. After the pipetting, further culture was performed for 24 hours and then the cell clusters were observed. The cells, medium, HA complex, culture conditions, and the like that were used herein were as follows. Furthermore, the type A wild-type HA complex and type A mutant HA complexes used herein were the same as those produced in Example 8.

<Cells>

Human iPS Cells (Tic (iPS cells that had been maintained in iMatrix-511 (nippi), NP19))

<Medium> mTeSR1 (STEMCELL Technologies)

<HA>

Type A Wild-Type HA Complex

Type A Mutant HA Complex 1 (HA1 N285A)

Type A Mutant HA Complex 2 (HA3 R528A)

Type A Mutant HA Complex 3 (HA1 N285A/HA3 R528A)

Type A Mutant HA Complex 4 (HA3 K607A)

<HA Preparing and Adding Method>

The HA complexes each were serially diluted with PBS and were further diluted using a medium (mTeSR1). This (final concentration: 100 nM) was added to the wells.

<Culture Conditions>

5% $CO_2$ atmosphere at 37° C.

<Observation>

Using In Cell Aanalyzer (trade name, manufactured by GE healthcare Bio-Sciences Corp.), the cell clusters were observed in the entire visual field.

As a control, the same procedure as described above was carried out, except that no HA complex was added.

The above results are indicated in Table 5 below.

TABLE 5

(Table 5)

| | | Mutation Site | Cluster Breakup Effect |
|---|---|---|---|
| Type A Wild-Type HA Complex | | — | ◎ |
| Type A Mutant | 1 | HA1 N285A | ◉ |
| HA Complex | 2 | HA3 R528A | ◉ |
| | 3 | HA1 N285A/ HA3 R528A | ◉ |
| | 4 | HA3 K607A | Δ |
| Control | | — | x |

[Evaluation Criteria]

◉: Cell clusters were able to be divided into further smaller blobs.
◎: Cell clusters were able to be divided into smaller blobs.
Δ: Division of cell clusters was hardly observed.
x: Cell clusters were not divided.

In the case of the type A wild-type complex, cell clusters were able to be broken up at a similar level to those of the type B wild-type HA complex and the type B mutant HA complexes 1 to 3. When the same concentration condition was used, the type A mutant HA complexes 1 to 3 were able to divide the cell clusters into further smaller blobs than those obtained in the cases of the type A wild-type complex, the type B wild-type HA complex, and the type B mutant HA complexes 1 to 3. On the other hand, when the mutant HA complex 4 (HA3 K607A) of Comparative Example 1, which is a cadherin-binding activity-deficient mutant, was added, division of the cell clusters was hardly observed, while the cell clusters were not divided in the case of the control (with no HA complex added).

[Sequence Listing Free Text]

SEQ ID NO 1: Subcomponent HA1 of wild-type hemagglutinin derived from *Clostridium botulinum* type B SEQ ID NO 2: Subcomponent HA2 of wild-type hemagglutinin derived from *Clostridium botulinum* type B SEQ ID NO 3: Subcomponent HA3 of wild-type hemagglutinin derived from *Clostridium botulinum* type B SEQ ID NO 4: Type B mutant HA1 (HA1 N286A)

SEQ ID NO 5: Type B mutant HA3 (HA3 R528A)

SEQ ID NO 6: Type B mutant HA3X (HA3 K607A)

SEQ ID NO 7: FLAG-tag

SEQ ID NO 8: Strep-tag

SEQ ID NOs 9 to 14: Primers

SEQ ID NO 15: D4-tag

SEQ ID NO 16: Subcomponent HA1 of wild-type hemagglutinin derived from *Clostridium botulinum* type A SEQ ID NO 17: Subcomponent HA2 of wild-type hemagglutinin derived from *Clostridium botulinum* type A SEQ ID NO 18: Subcomponent HA3 of wild-type hemagglutinin derived from *Clostridium botulinum* type A

The invention claimed is:

1. A mutant hemagglutinin complex protein comprising:

subcomponents HA1, HA2, and HA3 of hemagglutinin derived from *Clostridium botulinum* type B, in which at least an amino acid corresponding to asparagine at position 286 in an amino acid sequence of a wild type of the subcomponent HA1 and an amino acid corresponding to arginine at position 528 in an amino acid sequence of a wild type of the subcomponent HA3 are mutated;

an amino acid sequence constituting an E-cadherin binding site.

2. The mutant hemagglutinin complex protein according to claim 1, wherein the complex protein further comprises a subcomponent HA1 of hemagglutinin derived from *Clostridium botulinum* type B.

3. The mutant hemagglutinin complex protein according to claim 1, wherein the amino acid corresponding to asparagine at position 286 in the amino acid sequence of a wild type of the HA1 is substituted with alanine.

4. The mutant hemagglutinin complex protein according to claim 1, wherein the subcomponent HA1 is tagged at a C-terminal thereof.

5. A kit, comprising:

a medium component for a stem cell having pluripotency; and mutant hemagglutinin complex protein according to claim 3.

6. A mutant hemagglutinin complex protein comprising:

subcomponents HA1, HA2 and HA3 of hemagglutinin derived from *Clostridium botulinum* type B, in which at least an amino acid corresponding to asparagine at position 286 in the amino acid sequence of a wild type of the HA1 is mutated;

an amino acid sequence constituting an E-cadherin binding site.

7. A method for culturing a stem cell having pluripotency, the method comprising:

culturing the stem cell having pluripotency in the presence of the mutant hemagglutinin complex protein according to claim 6.

8. The method according to claim 7, wherein the culturing is performed by adhesion culture or suspension culture.

9. A method for removing a cell deviated from an undifferentiated state, the cell being a cell that has emerged or may possibly emerge during culture of a stem cell having pluripotency, the method comprising:

culturing the stem cell having pluripotency in the presence of the mutant hemagglutinin complex protein according to claim 6.

10. A method for maintaining an undifferentiated state of a stem cell having pluripotency, the method comprising:

culturing the stem cell having pluripotency in the presence of the mutant hemagglutinin complex of claim 6.

11. A method for culturing iPS cells of human origin, the method comprising:

culturing the iPS cells in suspension culture in the presence of the mutant hemagglutinin complex of claim 6.

12. The method according to claim 11, wherein the method comprises:

culturing a cell cluster of the iPS cells in suspension culture in the presence of hemagglutinin derived from *Clostridium botulinum* to divide the cell cluster into blobs, and culturing the blobs to form a new cell cluster in suspension culture, in the same medium as that in which the cell cluster is divided.

13. A method for dividing a cell cluster of iPS cells of human origin, the method comprising:

culturing the iPS cells in suspension culture in the presence of the mutant hemagglutinin complex of claim 6.

14. The method according to claim 11, wherein the hemagglutin derived from *Clostridium botulinum* is taken up by endocytosis.

15. The mutant hemagglutinin complex protein according to claim 14, wherein said amino acid corresponding to asparagine at position 286 in the amino acid sequence of a wild type of the HA1 is substituted with alanine.

16. The mutant hemagglutinin complex protein according to claim 14, wherein the subcomponent HA1 is tagged at a C-terminal thereof.

17. The mutant hemagglutinin complex protein according to claim 14, wherein the mutant hemagglutinin complex protein has an amino acid corresponding to arginine at position 528 in an amino acid sequence of a wild type of the subcomponent HA3 substituted with alanine.

18. A kit, comprising:

a medium component for a stem cell having pluripotency; and the mutant hemagglutinin complex protein according to claim 14.

* * * * *